(12) United States Patent
Regev et al.

(10) Patent No.: US 9,925,021 B2
(45) Date of Patent: Mar. 27, 2018

(54) DENTAL IMPLANT SYSTEMS AND METHODS FOR ACCESSING INTRA CAVITY AREAS THERETHROUGH

(76) Inventors: David Regev, Modiin-Macabim-Reut (IL); Moshe J. Weinberg, Beer-Sheva (IL); Ruth Weinberg, Tel Aviv (IL); David Polak, Mishmar Ayalon (IL); Yosef Rubinstein, Nes-Ziona (IL)

( * ) Notice: Subject to any disclaimer, the term of this patent is extended or adjusted under 35 U.S.C. 154(b) by 934 days.

(21) Appl. No.: 14/241,540

(22) PCT Filed: Aug. 29, 2012

(86) PCT No.: PCT/IL2012/050333
§ 371 (c)(1),
(2), (4) Date: Nov. 3, 2014

(87) PCT Pub. No.: WO2013/030835
PCT Pub. Date: Mar. 7, 2013

(65) Prior Publication Data
US 2015/0056569 A1 Feb. 26, 2015

Related U.S. Application Data

(60) Provisional application No. 61/528,419, filed on Aug. 29, 2011.

(51) Int. Cl.
*A61C 8/00* (2006.01)
*A61C 19/06* (2006.01)

(52) U.S. Cl.
CPC .......... *A61C 8/0022* (2013.01); *A61C 8/0018* (2013.01); *A61C 8/0068* (2013.01); *A61C 8/0092* (2013.01); *A61C 19/06* (2013.01)

(58) Field of Classification Search
CPC ... A61C 8/0022; A61C 8/0018; A61C 8/1168; A61C 8/0092; A61C 19/06
See application file for complete search history.

(56) References Cited

U.S. PATENT DOCUMENTS 4,021,921 A 5/1977 Detaille
4,252,525 A 2/1981 Child
(Continued)

FOREIGN PATENT DOCUMENTS

EP 1973977 A1 7/2008
KR 20070098219 A 10/2007
(Continued)

*Primary Examiner* — Heidi M Eide
(74) *Attorney, Agent, or Firm* — Browdy and Neimark, PLLC

(57) ABSTRACT

A method and a dental implant system for accessing selected intra-cavity locations there-through that includes: (a) a dental implant having a plurality of openings configured for being implanted in an intra-cavity area of a patient, wherein each one of the plurality of openings allows access from an external area of the dental implant to a space in the intra-cavity area between the implant and a jawbone of the patient, when the dental implant is installed in the intra cavity; and (b) one or more directing element that is removably securable to the dental implant, wherein the directing element includes openings and is configured to allow access to one or more specific locations at this space through a selected at least one of the plurality of openings of the dental implant, when secured thereto.

17 Claims, 24 Drawing Sheets

(56) References Cited

U.S. PATENT DOCUMENTS

| | | |
|---|---|---|
| 5,343,877 A | 9/1994 | Park |
| 6,939,135 B2 | 9/2005 | Sapian |
| 7,300,282 B2 | 11/2007 | Sapian |
| 2005/0251266 A1 | 11/2005 | Maspero |
| 2006/0036253 A1* | 2/2006 | Leroux ............... A61B 17/864 623/16.11 |
| 2006/0251896 A1 | 11/2006 | Ferencz |
| 2007/0016163 A1 | 1/2007 | Santini, Jr. |
| 2007/0081112 A1 | 4/2007 | Kitamura et al. |
| 2007/0105068 A1 | 5/2007 | Stucki-McCormick |
| 2007/0162024 A1 | 7/2007 | Siemonsmeier et al. |
| 2007/0208907 A1 | 9/2007 | Moore et al. |
| 2008/0095815 A1 | 4/2008 | Mao |
| 2008/0118893 A1* | 5/2008 | Armellini ............ A61K 9/0063 433/174 |
| 2009/0130167 A1 | 5/2009 | Shelton et al. |
| 2009/0304775 A1 | 12/2009 | Joshi et al. |
| 2010/0015196 A1 | 1/2010 | Kimble et al. |
| 2010/0055646 A1* | 3/2010 | Zhao .................... A61C 8/001 433/174 |
| 2010/0081112 A1* | 4/2010 | Better ................ A61C 8/0018 433/174 |
| 2010/0114174 A1* | 5/2010 | Jones ................ A61B 17/7098 606/279 |
| 2010/0196841 A1* | 8/2010 | Nahlieli ............... A61B 1/247 433/29 |
| 2010/0262089 A1* | 10/2010 | Sweeney ........... A61B 17/3472 604/272 |
| 2010/0266979 A1 | 10/2010 | Karmon |

FOREIGN PATENT DOCUMENTS

| | | |
|---|---|---|
| KR | 20100136848 A | 12/2010 |
| RO | 113205 B1 | 5/1998 |
| SE | 198909 | 10/1965 |
| WO | 2010106241 A2 | 9/2010 |
| WO | 2010131879 A2 | 11/2010 |
| WO | 2011092688 A1 | 8/2011 |
| WO | WO 2011/158193 * | 12/2011 ............ A61B 17/86 |

\* cited by examiner

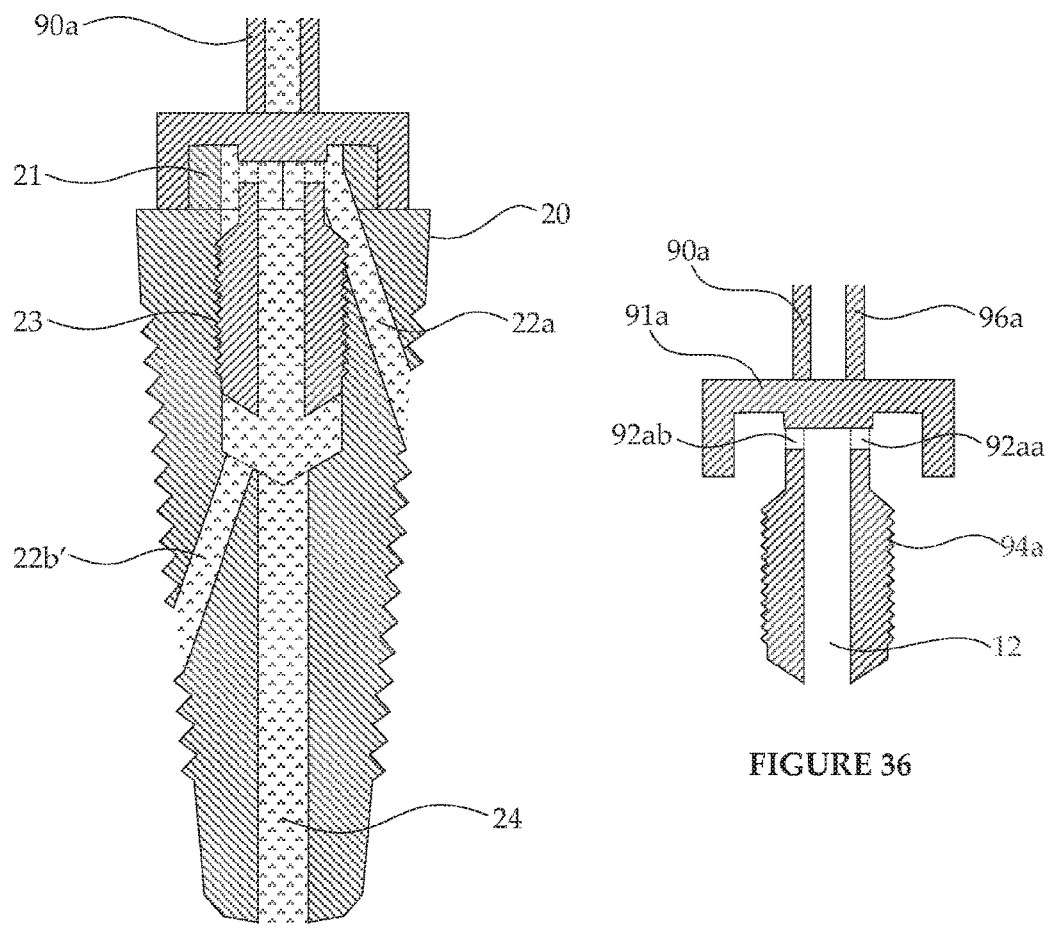
FIGURE 35
FIGURE 36
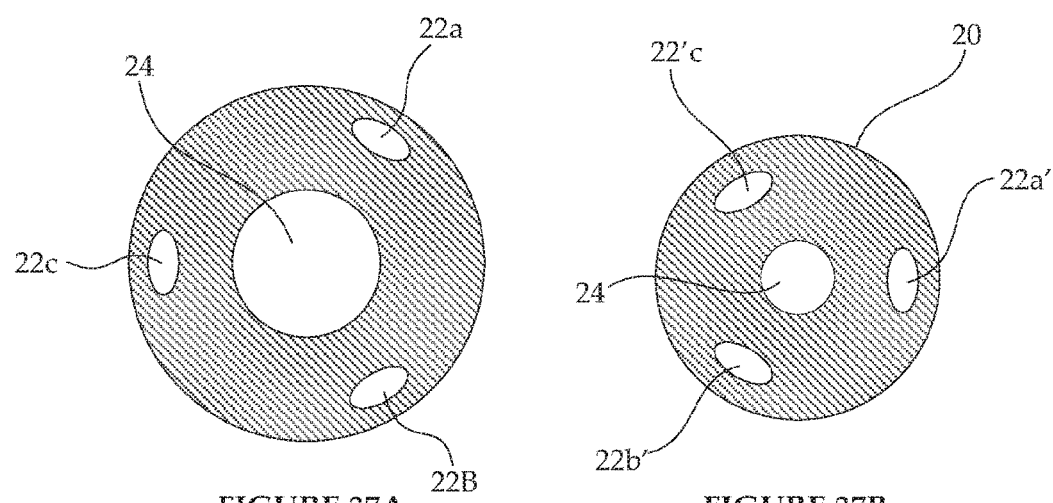
FIGURE 37A
FIGURE 37B

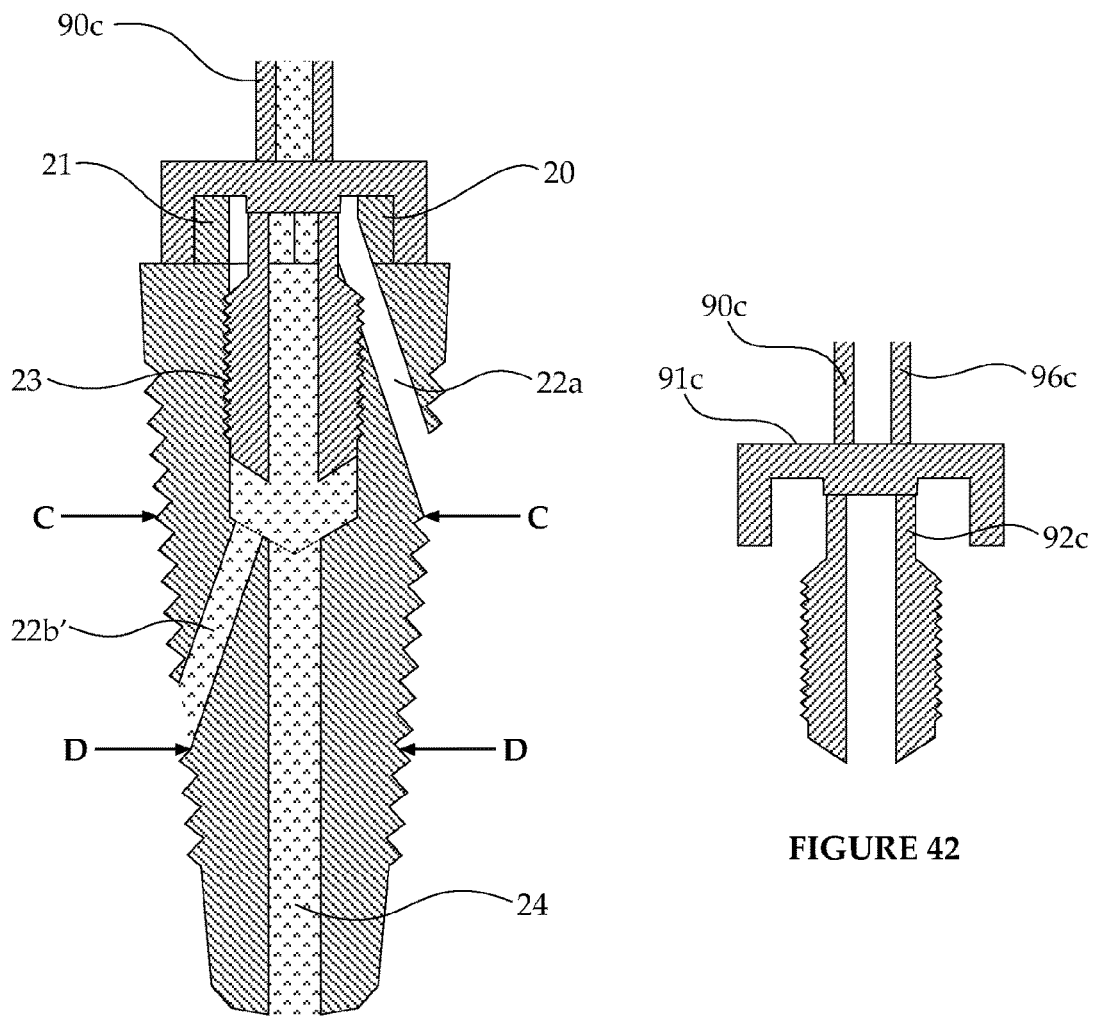
FIGURE 41
FIGURE 42
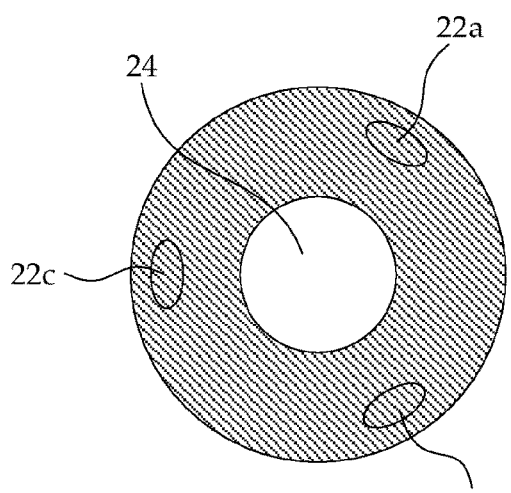
FIGURE 43A
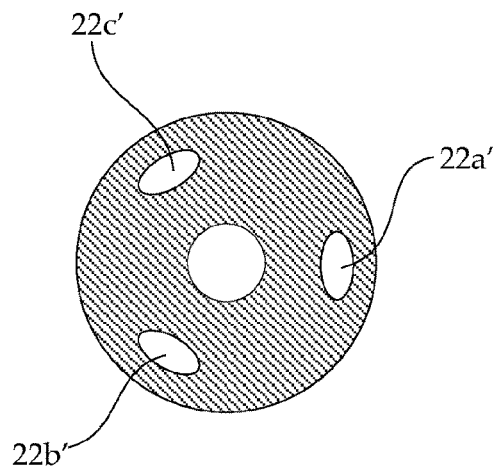
FIGURE 43B

DENTAL IMPLANT SYSTEMS AND METHODS FOR ACCESSING INTRA CAVITY AREAS THERETHROUGH

CROSS-REFERENCE TO RELATED PATENT APPLICATIONS

This application claims priority to Provisional patent application No. 61/528,419 filed on Aug. 29, 2011, which is incorporated herein by reference in its entirety.

FIELD OF THE INVENTION

The present invention relates to dental implants and systems including dental implants and methods for use thereof in intra-oral cavity dental procedures.

BACKGROUND OF THE INVENTION

Dental implants are often used for replacing damaged teeth and/or for facilitating in other dental procedures and installations. In some cases a dental implant is implanted in a tooth socket in which the original tooth have been removed or fell off long before the implant is placed.

In some cases, the bone tissue in the socket area of the implant must be recovered or built before the implant is placed requiring inserting bone morphogenetic materials to the alveolar bone for inducing osteogenesis of the alveolar bone in the socket area. This may be an extremely difficult task since it requires a surgical procedures and long healing period before implanting.

Patents and patent application such as US2009/0304775A1, KR20070098219 (A), RO 113205, WO 2010131879 (A2), KR20100136848, US2010/0081112, US2010/0196841, US2010/0266979, U.S. Pat. No. 5,915,967, US2008/0118893, US2007/0105068, US2007/0162024, U.S. Pat. No. 6,939,135, US2008/0095815, US2007/0016163, U.S. Pat. No. 7,300,282, SE000198909, US2009/0130167, U.S. Pat. No. 4,021,921, EP1943977, WO2010106241, US2009/0208907, U.S. Pat. No. 4,252,525, US2010/0015196, US2005/0251266 and U.S. Pat. No. 5,343,877, discuss various implant systems and methods of utilization thereof, some of which teach implants including a multiplicity of openings thereover for allowing directing of fluids therethrough for various purposes including for bone grafting.

SUMMARY OF THE INVENTION

According to some aspects of the present invention, there is provided a dental implant system for accessing selected intra-cavity locations there-through, comprising: (a) a dental implant having a plurality of openings, wherein the dental implant is configured for being implanted in an intra-cavity area of a patient, wherein each one of the plurality of openings allows access from an external area of the dental implant to a space in the intra-cavity area between the implant and a jawbone of the patient, when the dental implant is installed in the intra cavity; and (b) at least one directing element that is removably securable to the dental implant, wherein the directing element comprises at least one opening and is configured to allow access to at least one specific location in the space between the implant outer surface and the jawbone through a selected at least one of the plurality of openings of the dental implant, when secured thereto.

Optionally, the at least one directing element is configured to seal at least one of the openings of the respective dental implant, when secured thereto, for enabling access only through said selected at least one opening thereof.

Optionally, a plurality of directing elements are configured for being secured to the same dental implant, wherein each directing element thereof allows sealing at least one opening of the dental implant, where each directing element seals different openings of the dental implant.

Optionally, the dental implant comprises a main channel opening defining a main axis of the dental implant extending from a proximal to a distal ends thereof, and a plurality of channel openings each channel opening angularly extending from the main channel opening in an angle that is smaller than 90° to enable access to the intra-cavity area when using a tool.

According to some embodiments of the invention, the plurality of channel openings comprises groups of channel openings each group extends from the same plane, wherein the channel openings groups are located at a distance from one another along the main axis configured such that the main channel allows access from a distal end of the dental implant to each opening of each group to allow access therethrough to the intra-cavity space. This configuration allows filling the intra-cavity space with a material by first filling the intra-cavity areas that are further away from the proximal end of the implant from which the intra-cavity area is accessed and then gradually pushing the filling material towards the distal end of this space for optimal filling thereof as well as optimized access to the intra-cavity space when using a tool inserted through the proximal exposed end of the dental implant.

Optionally, the at least one directing element is further configured for increasing flow pressure of fluids directed through the openings towards at least one respective location at an external area of the dental implant.

Optionally, the dental implant comprises an outer threaded portion to allow enhancing the implant grip to the respective intra-cavity area in which it is implanted in.

Optionally, the dental implant comprises a connector for connecting to at least one directing element and other installations.

Additionally or alternatively, the dental implant comprises an inner screw-thread portion and the respective directing element comprises a compatible external screw-thread portion to allow the at least one directing element to be secured to the dental implant thereby. The dental implant system may further comprise a plurality of sealers for sealing each channel openings group of the dental implant thereby. According to some embodiments, each sealer may include a double layer plate made of a first layer comprising a first rigid material and a second layer comprising a material that is more elastic than the first material and has sealing capabilities to prevent infection.

Optionally, the dental implant system further comprises an instrument that is configured to removably connect to the directing element for allowing introducing pharmaceutical materials to areas located between the installed dental implant and the intra-cavity area by injecting this material using an injection tool into the location through the at least one selected opening using the dental implant having the respective directing element secured thereto. This dental implant system may also include a pressure controlling mechanism for measuring and controlling the pressure of the material introduced into the space through the instrument in the dental implant through the directing element.

According to other aspects of the invention, there is provided a method of accessing selected intra-cavity locations through a dental implant that comprises: (a) installing a dental implant comprising a plurality of openings at an intra-cavity area of a patient; (b) securing a directing element comprising at least one opening to the installed dental implant for selecting at least one of the openings of the dental implant for using thereof to carry out a dental procedure requiring access to a space of the intra-cavity area between the dental implant and a jawbone of the patient through the respective selected at least one opening; and (c) removing the directing element once the dental procedure is through.

Optionally, the procedure comprises directing a material through the directing element secured to the dental implant to selected at least one intra-cavity area. This material may comprise a bone-grafting material for enhancing bone-building, infection or disease therapy material or a cleansing fluid. The method may additionally include measuring and controlling pressure in the dental implant for allowing the material to be directed into the desired location at the intra-cavity area under a controlled pressure.

Optionally, the directing of this material comprises one of: (i) injecting this material by directing an injection tool through at least one of the openings of the dental implant available through the directing element secured thereto; (ii) inserting the material through said directing element under controlled pressure for allowing the material to reach the selected intra-cavity locations from the openings available through the directing element.

The method may further comprise cleansing an intra-cavity location that is located externally to the dental implant when installed, by using at least one mechanical cleansing device and directing it to the selected location through the selected opening.

According to some embodiments of the method, the dental implant is installed at a maxilla bone of a patient and is used for sinus membrane related medical procedures. The dental implant may be inserted into a designated bore at the maxilla bone of the patient, wherein a bone-grafting and/or material is inserted through the dental implant and the directing element secured thereto into a space created between the dental implant external surface portion and the lifted sinus membrane to lift this sinus membrane.

The method may further comprise sealing the dental implant once the directing element is removed by using a plurality of sealers for sealing a plurality of channel openings extending from a main opening of the dental implant, wherein each sealer comprises a double layer plate made of a first layer comprising a first rigid material and a second layer comprising a material that is more elastic than the first material.

The installing of the dental implant, securing the directing element and directing of the material through the openings may be carried out at an immediate implantation procedure in which the material is inserted through the implant into the space in the intra-cavity area between the dental implant and the jawbone of the patient at the time in which the installation (implantation) of the dental implant is carried out.

Additionally or alternatively, the directing of the material is carried out at a substantial period of time after the dental implant is installed such as months or years, wherein the directing element is used for directing the material through selected openings to access desired intra-cavity areas thereby.

BRIEF DESCRIPTION OF THE DRAWINGS

FIG. 35 is a transparent side view schematically illustrating the dental implant of FIG. 33 having a directing element secured thereto, according to some embodiments of the present invention;

FIG. 36 is a side view schematically illustrating the directing element of FIG. 35, according to some embodiments of the present invention;

FIG. 37A is an elevated cross sectional view showing cross section C-C of the dental implant shown in FIG. 36 directing element secured thereto, according to some embodiments of the present invention;

FIG. 37B is an elevated cross sectional view showing cross section D-D of the dental implant shown in FIG. 36 directing element secured thereto, according to some embodiments of the present invention;

FIG. 41 is a transparent side view schematically illustrating the dental implant of FIG. 33 having a directing element secured thereto, according to some embodiments of the present invention;

FIG. 42 is a side view schematically illustrating the directing element of FIG. 41, according to some embodiments of the present invention;

FIG. 43A is an elevated cross sectional view showing cross section C-C of the dental implant shown in FIG. 36 directing element secured thereto, according to some embodiments of the present invention;

FIG. 43B is an elevated cross sectional view showing cross section D-D of the dental implant shown in FIG. 36 directing element secured thereto, according to some embodiments of the present invention;

DETAILED DESCRIPTION OF SOME EMBODIMENTS OF THE INVENTION

Figure 1:
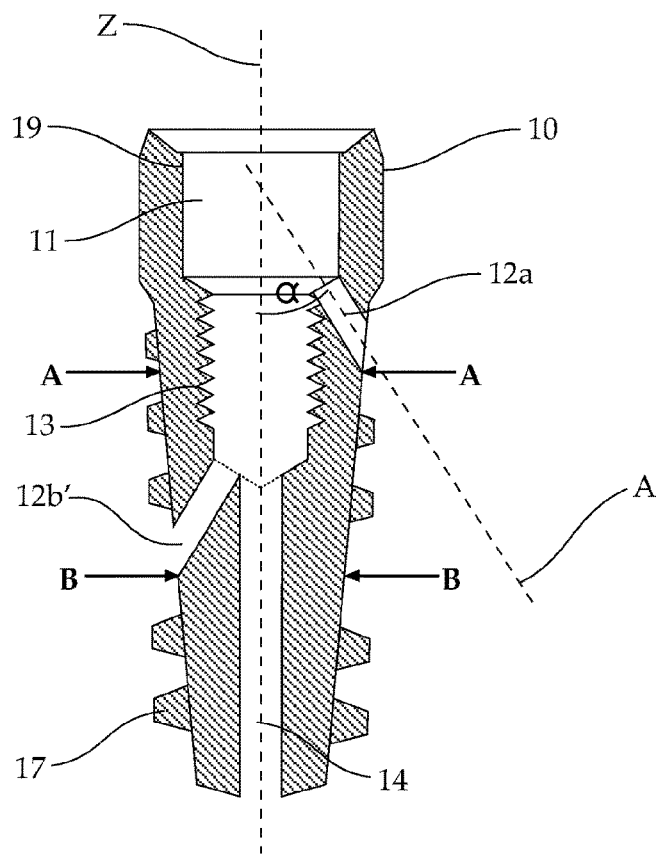
FIG. 1 is a transparent side view schematically illustrating a dental implant having a hexagonal internal connection and a multiplicity of openings, according to some embodiments of the present invention.

In the following detailed description of various embodiments, reference is made to the accompanying drawings that form a part thereof, and in which are shown by way of illustration specific embodiments in which the invention may be practiced. It is understood that other embodiments may be utilized and structural changes may be made without departing from the scope of the present invention.

The present invention, in some embodiments thereof, provides dental implant systems and methods for accessing selected intra-cavity locations of a patient located underneath the implanted, by accessing these locations through the implant itself without having to remove the implant to access these locations.

According to some embodiments of the invention, there is provided a dental implant system including a dental implant that includes a plurality of openings enabling access therethrough from one side thereof (e.g. the side(s) of the implant that typically connects to the dental abutment and/or cap) to oral intra-cavity areas such as the gum tissue and/or the jawbone located behind some portion of the implant. The system further includes one or more directing elements; each directing element can be secured to the dental implant in a removable manner, during, immediately or sometime after the implantation of the dental implant.

According to some embodiments of the invention, each directing element allows access from the dental implant to the desired specific location or spot in the oral intra-cavity area located behind a portion of the implant, when the directing element is secured thereto, only through selected one or more of the dental implant's openings, depending upon the specific configuration of the specific directing element.

For each dental implant design, a multiplicity of different directing elements may be adapted and used, each allowing access through different openings of the same implant for directing a tool or a bone-building fluid, for instance, to different locations in the oral intra-cavity area of a patient having the respective implant installed in his/her mouth right after the implant's installation or some time after (e.g., a few days or a few months).

According to some embodiments, the dental implant may be configured for being implanted in an intra-cavity area of a patient such as a tooth socket in a patient's maxilla and/or mandible, where the opening(s) selected to be used is(are) determined according to the physical configuration of the specific directing element in respect to the configuration of the dental implant and the location of each of its openings and the desired procedure that is to be implemented (e.g. cleansing of a specific location in the tooth socket, accessing a specific location for injecting bone-morphogenetic materials for bone grafting and the like).

The directing element may facilitate in at least one of: (i) enabling accessing only to one or more of the openings while sealing other openings to only allow access to some desired locations through these corresponding openings; and (ii) enabling to better control flow pressure of materials that are directed thereby from the dental implant to a tooth socket in which it is installed. This may be extremely useful when the procedure requires introducing fluid materials (e.g. bon morphogenetic materials) by simply pouring the fluids into the directing element allowing the fluid to only reach the areas through the open passageways of the directing element and preventing it from reaching other areas by sealing undesired openings of the implant.

For example, the directing element may seal one or more of the openings of the dental implant, when secured thereto, and leave only one or more other openings open. This will allow determining the intra cavity areas underneath the dental implant that can be accessed through the main opening. In this way, a single dental implant can be used for being implanted in any one or more suitable tooth sockets of a patient in any of the patient's maxilla and/or mandible while selecting a suitable directing element allowing access only to areas that correspond to the medical condition and desired procedure. This means, for example, that when one side of the tooth socket area underneath the implant has bone loss and the other side does not require bone building than the openings directing the healthy side may be sealed while only those directing to the relevant side(s) may be left open by using a directing element that seals the desired openings.

The directing element may be secured to the implant for using thereof in procedures involving directing of pharmaceutical materials through the specific openings such as bone morphogenetic, and/or therapeutic materials.

To allow the various possible directing element configurations (e.g. all the possible number of open openings vs. the closed openings), each dental implant may be compatible to a multiplicity of directing elements each directing element configured to allow access through different openings of the specific corresponding dental implant meaning each directing element allows sealing different openings.

A distal portion of the dental implant is designated for being implanted inside a tooth socket or anywhere else inside a part of a patient's jawbone such as through a specially perforated thread therein. At least part of the first portion of the dental implant is designated for receiving of another construction such as an abutment, a bridge and the like. To carry out a dental implantation, a female threaded portion is typically drilled in a jawbone area of the tooth socket. The depth of the drilled portion mainly depends on the condition, thickness/depth and/or type of the bone tissue in that area. Some patients have a serious bone depletion allowing only a very short threaded portion to be drilled and used for anchoring the implant in the dental primer stabilization process before the bone tissue underneath the implant can be recovered.

The access to specific predetermined openings can be used, for example, for directing materials (such as sedative, bone morphogenetic, and/or therapeutic materials) inserted through the main opening only to selected and predetermined areas in the intra-cavity area of the patient in which the dental implant is installed. For example, in ossification procedures requiring accessing areas between the outer surface of the dental implant and the tooth socket areas lacking bone tissue for introducing bone filling and constructing (inductive) materials, the systems allow easy and comfortable access only to those desired intra-cavity areas once the dental implant is already installed.

The term "patient" may refer to any gnathostomata such as a human, a mammal, etc.

The term "dental implant" refers to any type of dental devices that are inserted into the jawbone. It can be used to replace one and/or a multiplicity of teeth-roots abutment or for other functions.

The openings may be configured in a manner that is adapted to the configuration of the directing elements and also for allowing sealers to be placed after treatments, to prevent infection. The directing elements are configured according to the design and configuration of the dental implant and its openings locations as well as according to the openings it should seal when installed to the directing element. Each directing element is further configured to allow optimal compatibility with the dental implant and its openings design. For example, the dental implant may include angular channel openings extending from a main vertical opening, where each set of channel openings angularly extends from a different level (e.g. height) of the vertical main opening channel. This allows adapting the directing elements according to the level from which each set of openings extends.

Figure 2A:
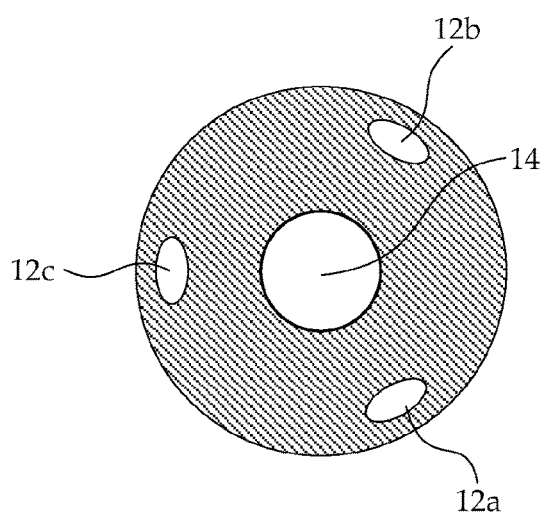
FIG. 2A is an elevated cross sectional view schematically illustrating section A-A of the dental implant of FIG. 1.
Figure 2B:
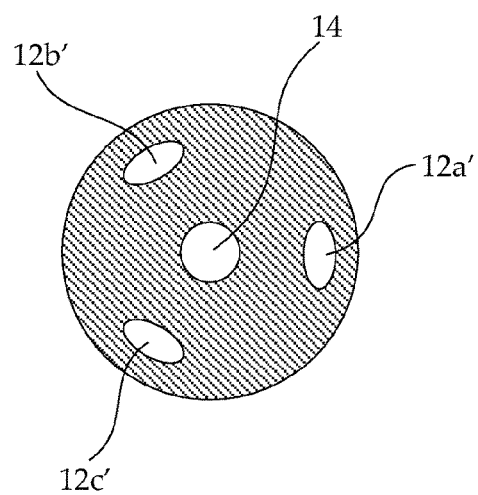
FIG. 2B is an elevated cross sectional view schematically illustrating section B-B of the dental implant of FIG. 1.

Reference is now made to FIGS. 1, 2A and 2B, schematically illustrating a side view and an elevated view of a dental implant 10 with a main opening 19 having a hexagonal internal connection, according to some embodiments of the present invention.

Dental implant 10 includes a main opening 19 that extends vertically through a vertical axis "z" all through the inner body of the dental implant 10 creating three main portions: a first portion 11 having a polygonal recess shape, a second (central) portion 13 and a third portion 14. Second portion 13 has a threaded inner walling for receiving and securing abutments, caps and the like and optionally directing elements.

Six channel openings 12a, 12b, 12c and 12a', 12b', 12c' extend from two different levels of main opening 19 enabling access therefrom to multiple locations outside implant 10. First portion 11 of main opening 19 is located at a first portion of dental implant 10 and second and third portions 13 and 14 of main opening 19 as well as channel openings 12a, 12b, 12c and 12a', 12b', 12c' are carved through another portion of dental implant 10. First portion 11 of main opening 19 allows access thereto when implant 10 is installed (implanted) into the tooth socket or any other part in the jawbone.

Each of the openings 12a, 12b, 12c and 12a', 12b', 12c' allows access from the main opening 19 of dental implant 10 to a different location/area of the space between tooth socket and implant's external 10 surface when implanted therein.

To improve access to various intra-cavity locations, each group of channel openings extract from the same plane and optionally also ends at the same plane. For example, a first group of openings 12a, 12b, 12c begin at one first plane and a second group of openings 12a', 12b', 12c' begin at a second plane located at a distance from the first plane along axis "z". Additionally, each opening is configured as a channel that angularly extends from main opening 19 towards a different direction. This configuration of the openings 11-12c' allows covering a large three-dimensional external area of implant 10 to allow easy and accurate accessing thereto.

In this way, a multiplicity of channel openings groups may be set along the main axis of the dental implant, where each group of channel openings extends from the same plane. According to some embodiments, the channels are angular in respect to the main axis in an angle that is smaller than 90°. According to some embodiments, the distance between the planes from which each group extends is determined according to the number of channel openings groups. This configuration gives several advantages such as: (i) easy access to distal areas in the intra-cavity of the patient when using mechanical tools such as a file inserted through a proximal exposed end of the implant; and (ii) for enabling filling the intra-cavity space between the jawbone behind the implant and the external surface of the implant with materials such as bone-grafting materials by first filling the intra-cavity areas that are further away from the proximal end of the implant from which the intra-cavity area is accessed and then gradually pushing the filling material towards the distal end of this space for optimal filling thereof.

For example, as illustrated in FIG. 1, channel opening 12a forms an angle α between the vertical axis z and a channel 12a main axis A thereof, where α<90° preferably yet not necessarily α<90°. The angle α allows easy and comfortable access from main opening 19 first portion 11 to the tooth socket when using, for instance, an elongated tool for accessing the socket therethrough such as a syringe, a cleaning needle, a tube structure, an endodontic file, an ultrasonic scaling device and the like.

The dental implant 10 illustrated in FIGS. 1-3, 5-7, 9-12, 14-16, 18-20, 22-24, 26-27 and 48-49, has a polygonal-hexagonal recess portion (internal hexagonal connection) mainly configured for receiving a compatible polygonal-hexagonal protruding portion of an abutment as well as of directing element and/or any other components used in dental procedures that include securing these components to the dental implant.

Reference is now made to FIGS. 3-6, schematically illustrating a dental system including dental implant 10 and a directing element 50a, according to some embodiments of the present invention. Directing element 50a is configured to be secured to dental implant 10 by screwing a male threaded portion of a second part 53a of directing element 50a to a corresponding female screw thread in the second portion 13 of dental implant 10. Directing element 50a does not seal any of the openings 12a-12c, 12a'-12c' and/or 19 but rather serves to improve pressure control when injecting and/or pouring pharmaceutical materials therethrough. Directing element 50a includes an elongated member 56a having an open passageway 55a perforated therethrough having threaded portions such as 53a and at its edges and a second member 51a configured to be received by hexagonal opening in portion 11. Threaded portion 53a is configured to be screwed to portion 13 threaded part for removably securing directing element 50a to dental implant 10.

Figure 3:
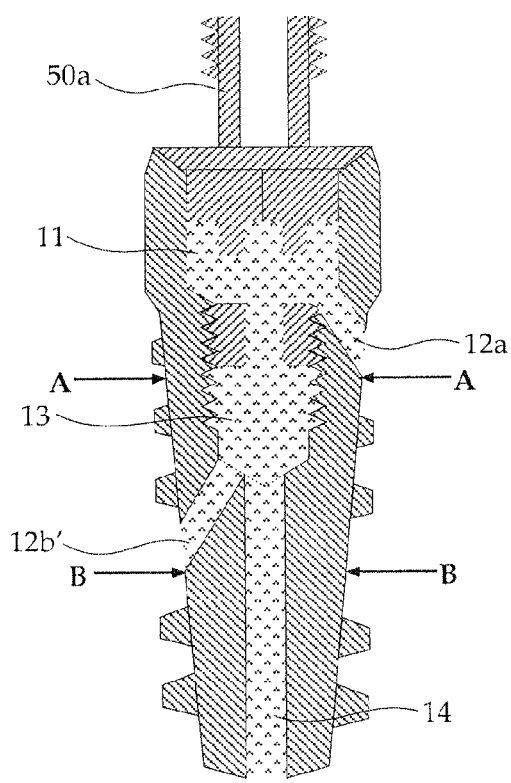
FIG. 3 is a transparent side view schematically illustrating the dental implant of FIG. 1 having a directing element secured thereto, according to some embodiments of the present invention.
Figure 4:
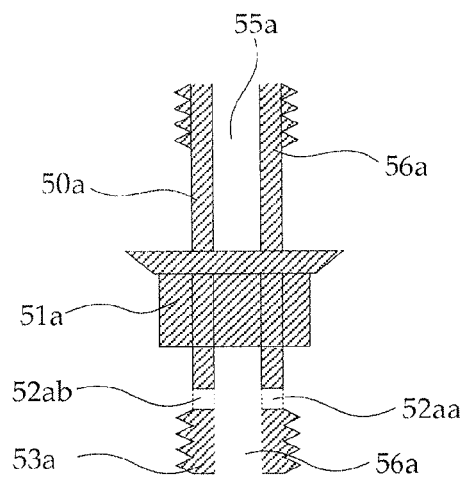
FIG. 4 is a side view schematically illustrating the directing element of FIG. 3, according to some embodiments of the present invention.
Figure 5:
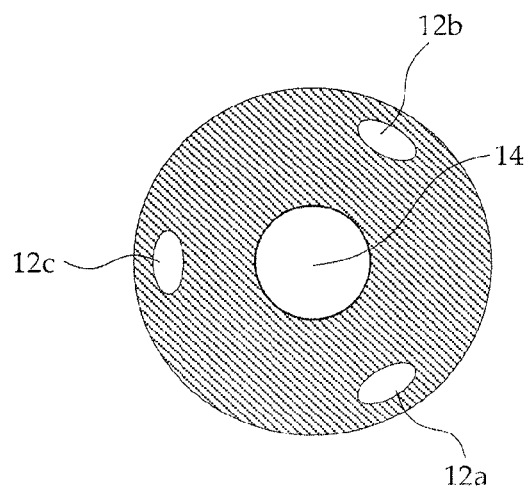
FIG. 5 is an elevated cross sectional view showing section A-A having a first set of channel openings of the dental implant and directing element secured thereto, according to some embodiments of the present invention.
Figure 6:
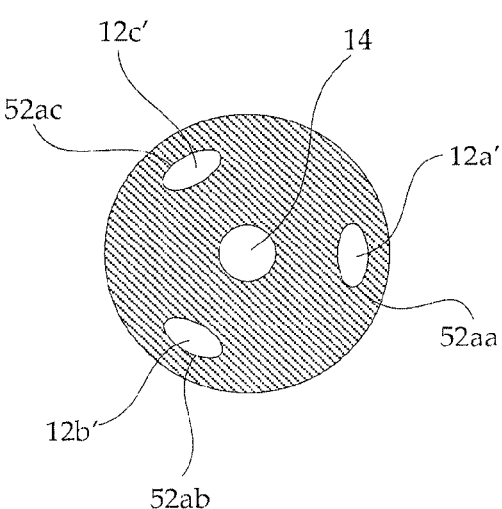
FIG. 6 is an elevated cross sectional view showing section B-B having a first set of channel openings of the dental implant and directing element secured thereto, according to some embodiments of the present invention.
Figure 7:
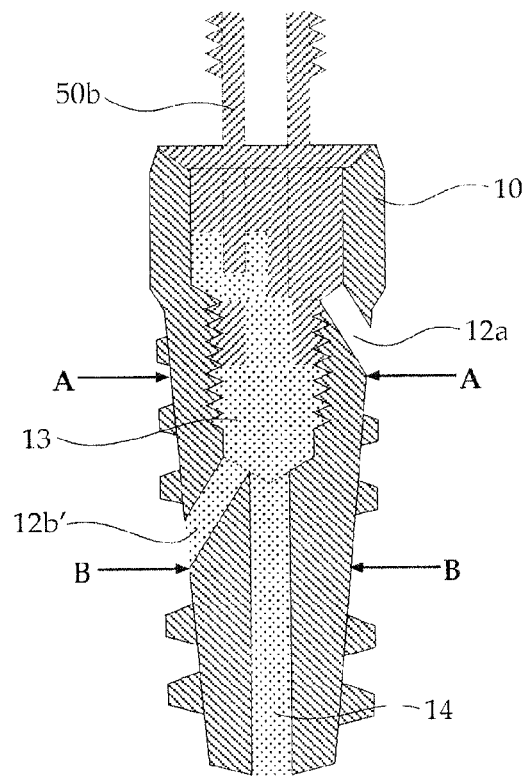
FIG. 7 is a transparent side view schematically illustrating the dental implant of FIG. 1 having a directing element secured thereto, according to some embodiments of the present invention.
Figure 8:
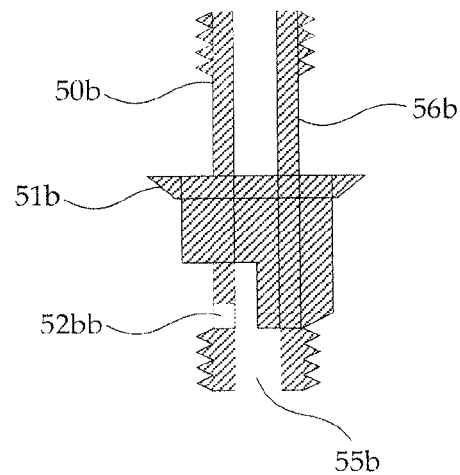
FIG. 8 is a side view schematically illustrating the directing element of FIG. 7, according to some embodiments of the present invention.

As shown in FIGS. 3-6, directing element 50a further includes between one and three side openings such as openings 52aa, 52ab, and 52ac, which allow access through openings 12a, 12b and 12c, and an additional fourth opening 55a, which allows leaving the entire second and third portions 13 and 14 along with openings 12a', 12b' and 12c' open, when directing element 50a is secured to dental implant 10. There number and/or size of the openings of directing member 50a does not have to be identical to the number of desired openings out of 12a-12c' and/or openings size but rather configured to allow the desired openings to be open and the desired closed openings to be sealed. As shown in FIGS. 3-4, the directing element 50a may further include an elongated member 56a connected to first part 51a for allowing easy access from the oral cavity of the patient into cavity 55a. A portion of the elongated member 56a may include an external male screw thread for allowing connecting other tools and elements to the directing element therethrough.

Figure 9:
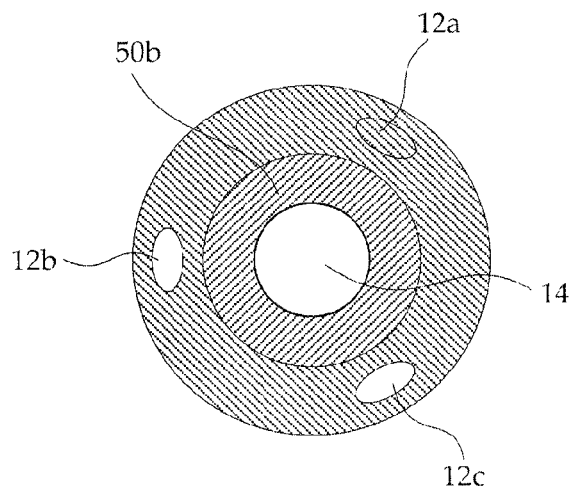
FIG. 9 is an elevated cross sectional view showing section A-A having a first set of channel openings of the dental implant and directing element secured thereto, according to some embodiments of the present invention.
Figure 10:
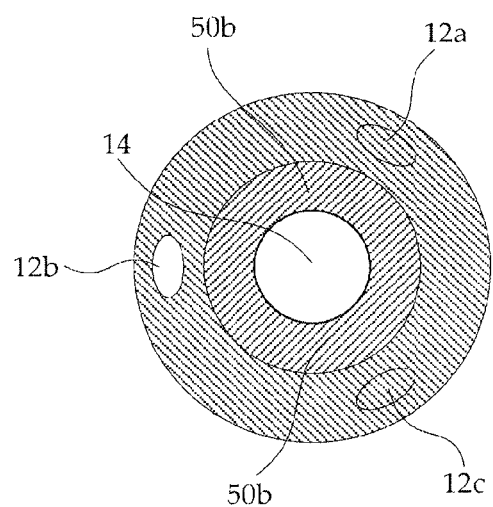
FIG. 10 is an elevated cross sectional view showing section A-A of the dental implant having a first set of channel openings of the dental implant and directing element secured thereto, according to some embodiments of the present invention.
Figure 11:
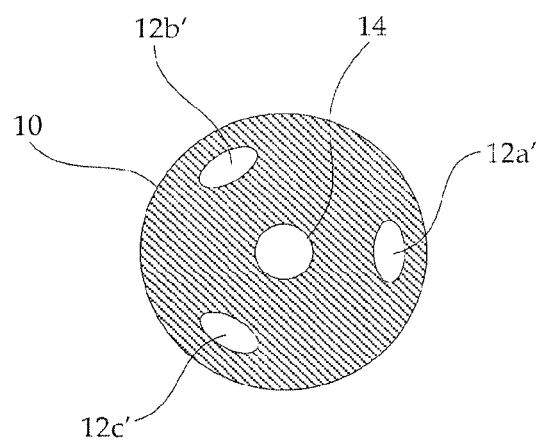
FIG. 11 is an elevated cross sectional view showing section B-B having a first set of channel openings of the dental implant and directing element secured thereto, according to some embodiments of the present invention.
Figure 12:
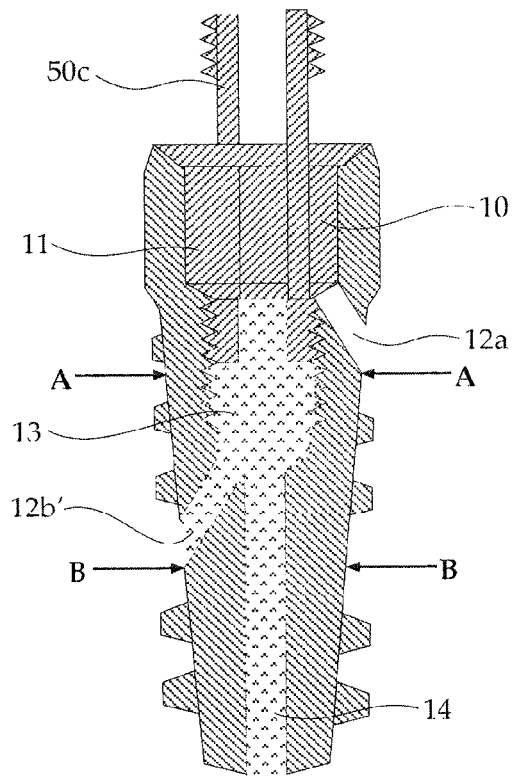
FIG. 12 is a transparent side view schematically illustrating the dental implant of FIG. 1 having a directing element secured thereto, according to some embodiments of the present invention.
Figure 13:
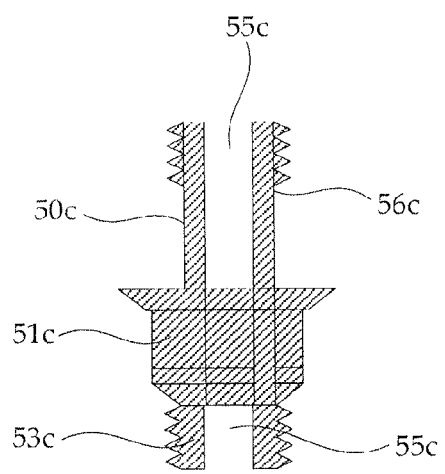
FIG. 13 is a side view schematically illustrating the directing element of FIG. 12, according to some embodiments of the present invention.
Figure 14:
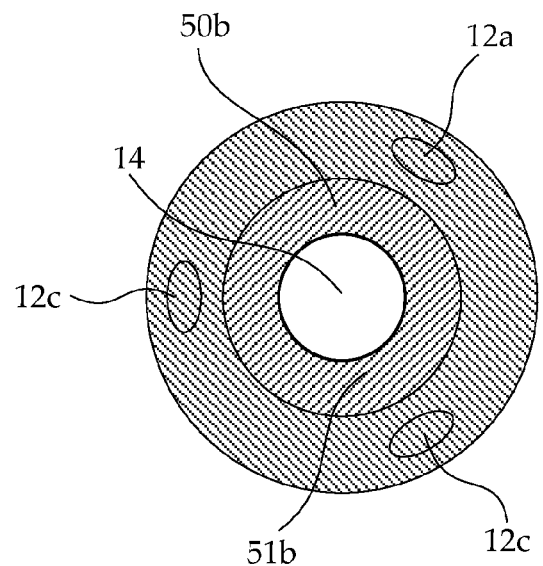
FIG. 14 is an elevated cross sectional view showing section A-A having a first set of channel openings of the dental implant and directing element secured thereto, according to some embodiments of the present invention.
Figure 15:
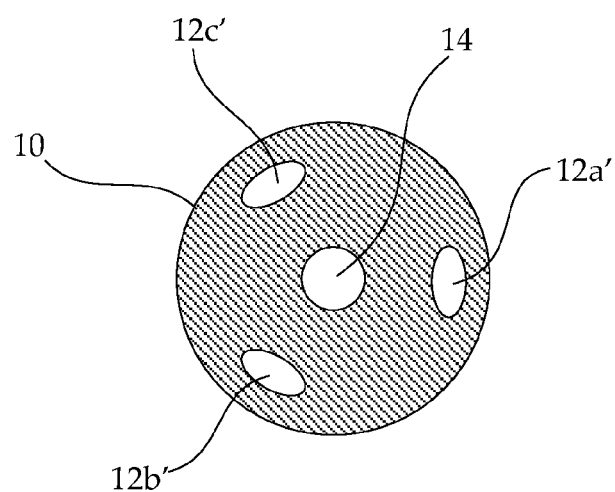
FIG. 15 is an elevated cross sectional view showing section B-B having a first set of channel openings of the dental implant and directing element secured thereto, according to some embodiments of the present invention.
Figure 16:
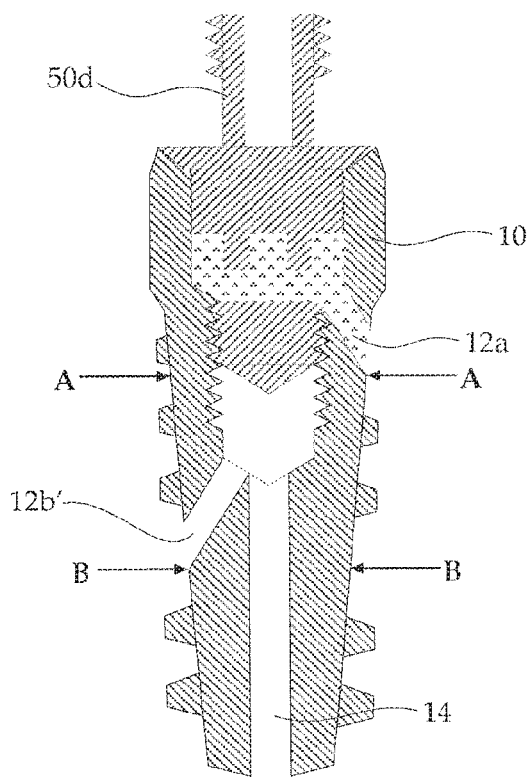
FIG. 16 is a transparent side view schematically illustrating the dental implant of FIG. 1 having a directing element secured thereto, according to some embodiments of the present invention.
Figure 17:
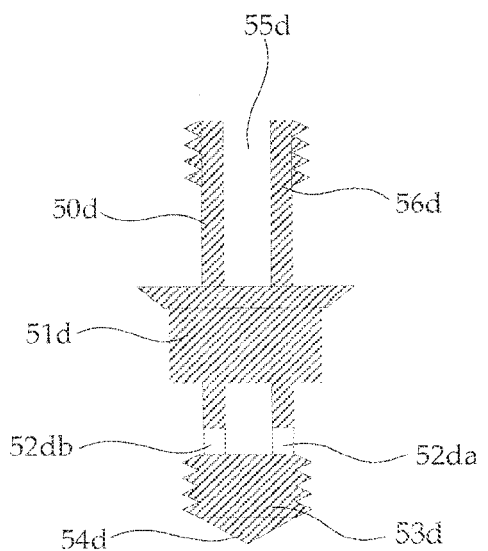
FIG. 17 is a side view schematically illustrating the directing element of FIG. 16, according to some embodiments of the present invention.
Figure 18:
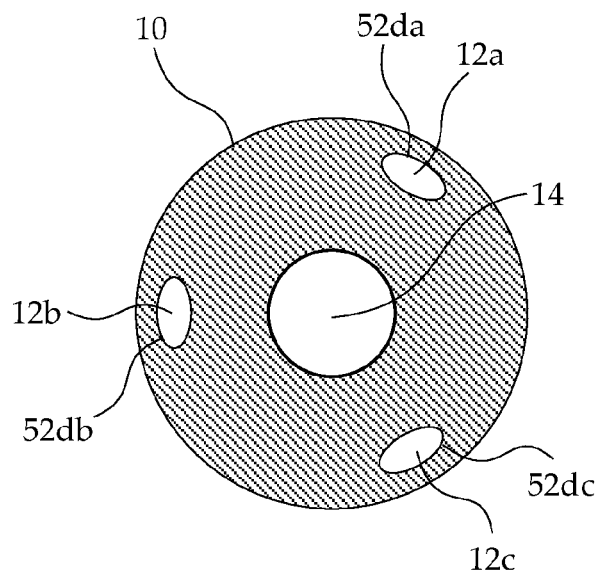
FIG. 18 is an elevated cross sectional view showing section A-A having a first set of channel openings of the dental implant and directing element secured thereto, according to some embodiments of the present invention.
Figure 19:
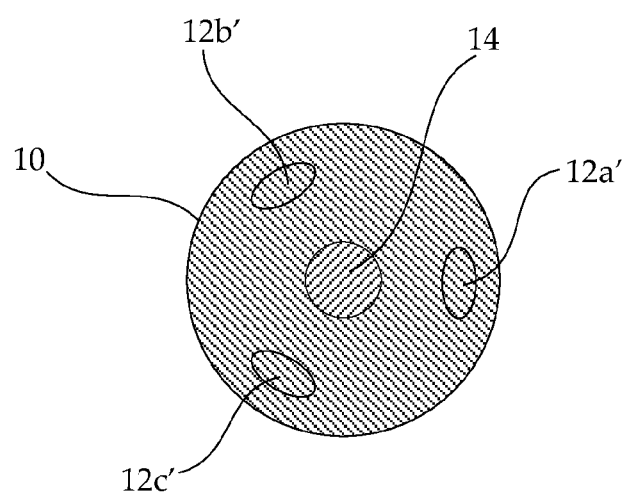
FIG. 19 is an elevated cross sectional view showing section B-B having a first set of channel openings of the dental implant and directing element secured thereto, according to some embodiments of the present invention.
Figure 20:
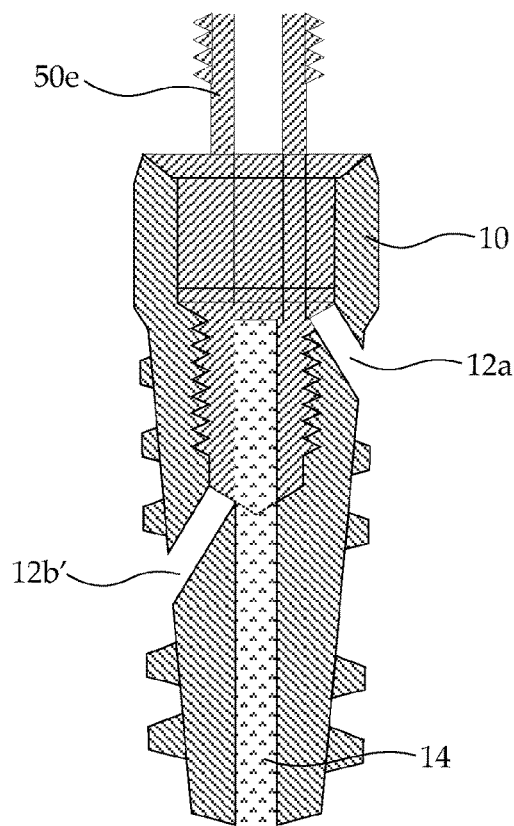
FIG. 20 is a transparent side view schematically illustrating the dental implant of FIG. 1 having a directing element secured thereto, according to some embodiments of the present invention.
Figure 21:
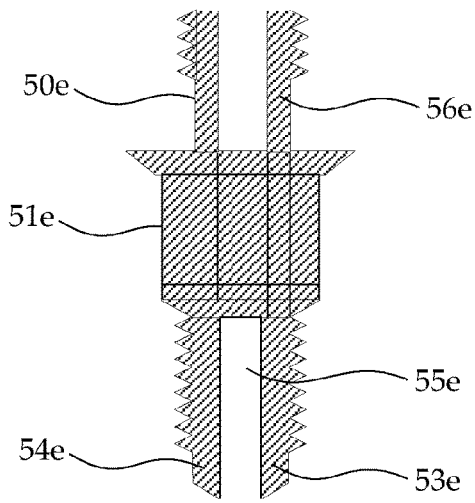
FIG. 21 is a side view schematically illustrating the directing element of FIG. 20, according to some embodiments of the present invention.
Figure 22:
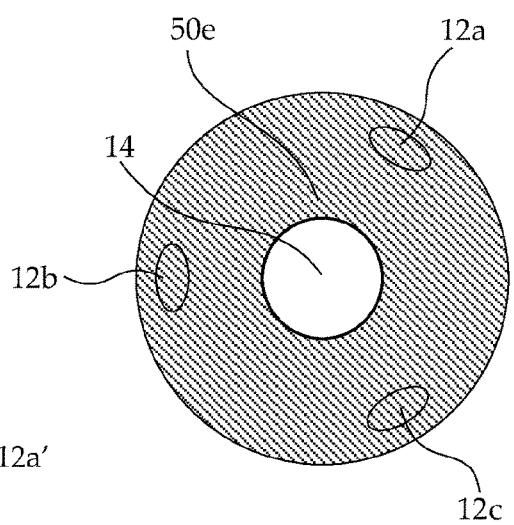
FIG. 22 is an elevated cross sectional view showing section A-A having a first set of channel openings of the dental implant and directing element secured thereto, according to some embodiments of the present invention.
Figure 23:
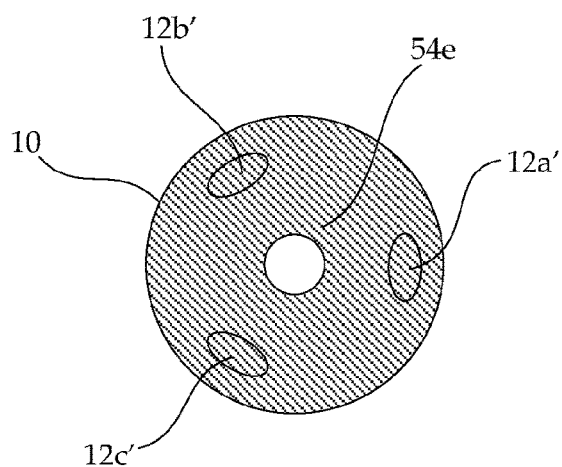
FIG. 23 is an elevated cross sectional view showing section B-B having a first set of channel openings of the dental implant and directing element secured thereto, according to some embodiments of the present invention.
Figure 24:
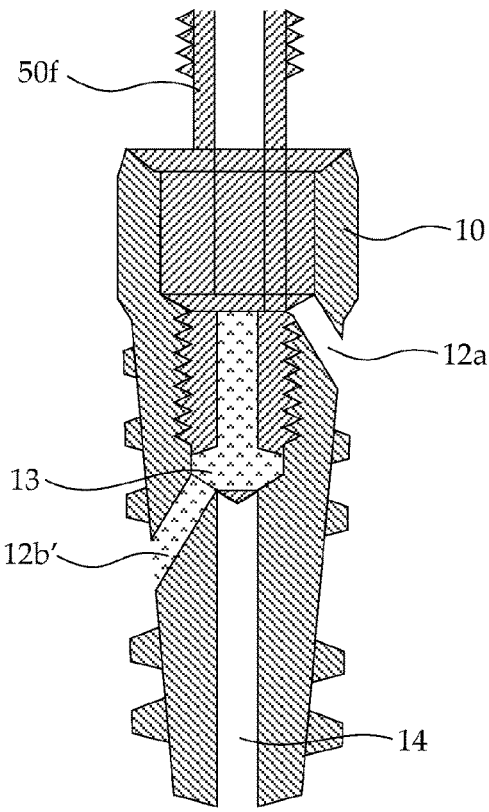
FIG. 24 is a transparent side view schematically illustrating the dental implant of FIG. 1 having a directing element secured thereto, according to some embodiments of the present invention.
Figure 25:
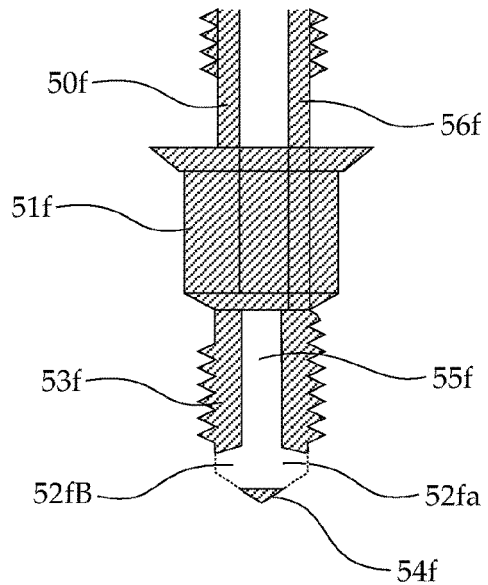
FIG. 25 is a side view schematically illustrating the directing element of FIG. 24, according to some embodiments of the present invention.
Figure 26:
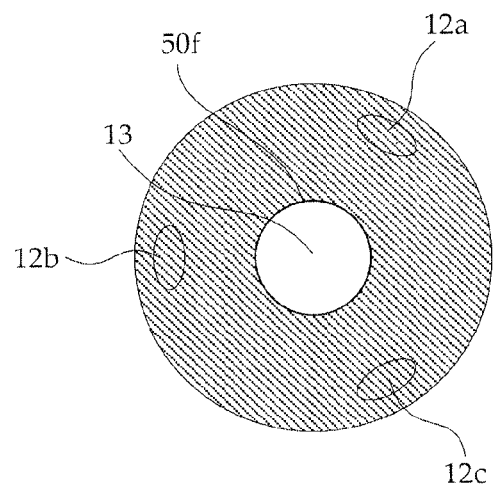
FIG. 26 is an elevated cross sectional view showing section A-A having a first set of channel openings of the dental implant and directing element secured thereto, according to some embodiments of the present invention.
Figure 27:
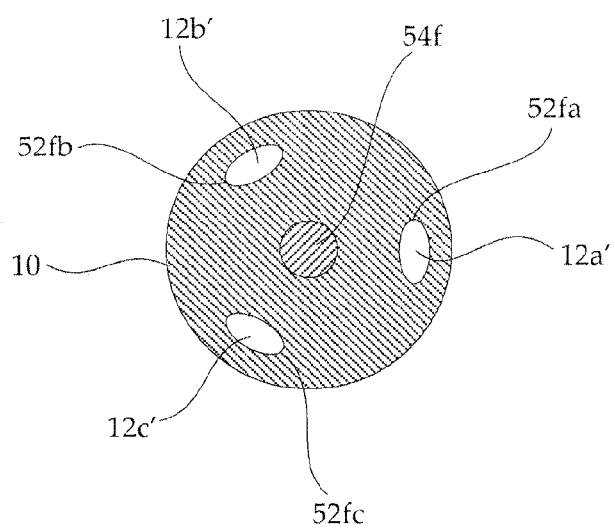
FIG. 27 is an elevated cross sectional view showing section B-B having a first set of channel openings of the dental implant and directing element secured thereto, according to some embodiments of the present invention.

FIGS. 7-11 schematically illustrate a dental system including dental implant 10 and another type of a directing element 50b, according to additional or alternative embodiments of the present invention. Directing element 50b allows sealing one or two of openings 12a-12c while leaving openings 12a', 12b', 12c' open and all through main opening 19. Second member 51b may enable either sealing access to opening 12a of dental implant 10 as illustrated in FIG. 9 or sealing openings 12a and 12c of the dental implant, as shown in FIG. 10. Directing element 50b includes at least one opening 52bb for leaving opening 12b accessible where opening 55b thereof allows access through openings 13, 14,12a', 12b' and 12c'.

Reference is now made to FIGS. 12-15, schematically illustrating dental implant 10 and another type of a directing element 50c, according to additional or alternative embodiments of the present invention. Directing element 50c allows sealing openings 12a-12c while leaving openings 14, 12a'-12c' open, when directing element 50c is secured to dental implant 10. Directing element 50c includes a first elongated member 56c having an opening there through 55c a threaded portion 53c that is similar to those parallel parts of directing elements 50a. Directing element 50c further includes an external threaded portion for securing thereof to another tool/instrument such as a syringe and the like. Directing element 50c also includes a polygonal (hexagonal) member 51c for fitting into polygonal recess 11 of implant 10.

Reference is now made to FIGS. 16-19, schematically illustrating dental implant 10 and another type of a directing element 50d, according to additional or alternative embodiments of the present invention. Directing element 50d allows sealing openings 12a'-12c' and 14 and has openings 52da, 52db, and 52dc to provide access to openings 12a-12c. Directing element 50d includes an elongated first member 56d having an opening 55d there through and a second member 51d that are similar to those parallel parts of directing elements 50a, yet the threaded portion 53d of directing element 50d is sealed by a sealer 54d.

Reference is now made to FIGS. 20-23, schematically illustrating dental implant 10 and another type of a directing element 50e, according to additional or alternative embodiments of the present invention. Directing element 50e allows sealing openings 12a-12c and openings 12a'-12c' while leaving only the opening 14 in the third portion open. Directing element 50e includes an elongated first member 56e including an opening 55e perforated there through that is similar to those parallel parts of directing elements 50c, yet a threaded portion 53e of directing element 50e is elongated enough to seal openings 12a-12c and includes an angular rim portion 54e at its edge that allows sealing openings 12a'-12c' when directing element 50e is secured to dental implant 10. Directing element 50e also includes a polygonal member 51e for fitting into polygonal recess 11 of implant 10.

Reference is now made to FIGS. 24-27, schematically illustrating dental implant 10 and another type of a directing element 50f, according to additional or alternative embodiments of the present invention. Directing element 50f allows sealing openings 12a-12c and the opening 14 of dental implant 10, while leaving openings 12a'-12c' open. Directing element 50f includes an elongated first member 56f having opening 55f and a second member 51f that are similar to those parallel parts of directing elements 50e, yet a threaded portion 53f of directing element 51f is elongated enough to seal openings 12a-12c and includes one or more openings 52fa (and 52fb52fc), which allow material flow through 12a'-12c' openings. Directing element 50f further includes another sealer 54f that allows sealing opening 14, when directing element 50f is secured to dental implant 10.

The hexagonal configuration of both the receiving openings 11 of dental implant 10 and the protruding portion 51a-51f of directing elements 50a-50f allow discrete orientation of the directing element in relation to implant 10. This means that the directing element can be positioned in six different discrete predefined rotational angles in relation to a main axis extending along the main opening of dental implant 10, when secured thereto, which allows determining the sealed openings according to the directing element configuration as well as according to the rotation angle in which it is secured to dental implant 10.

Figure 28:
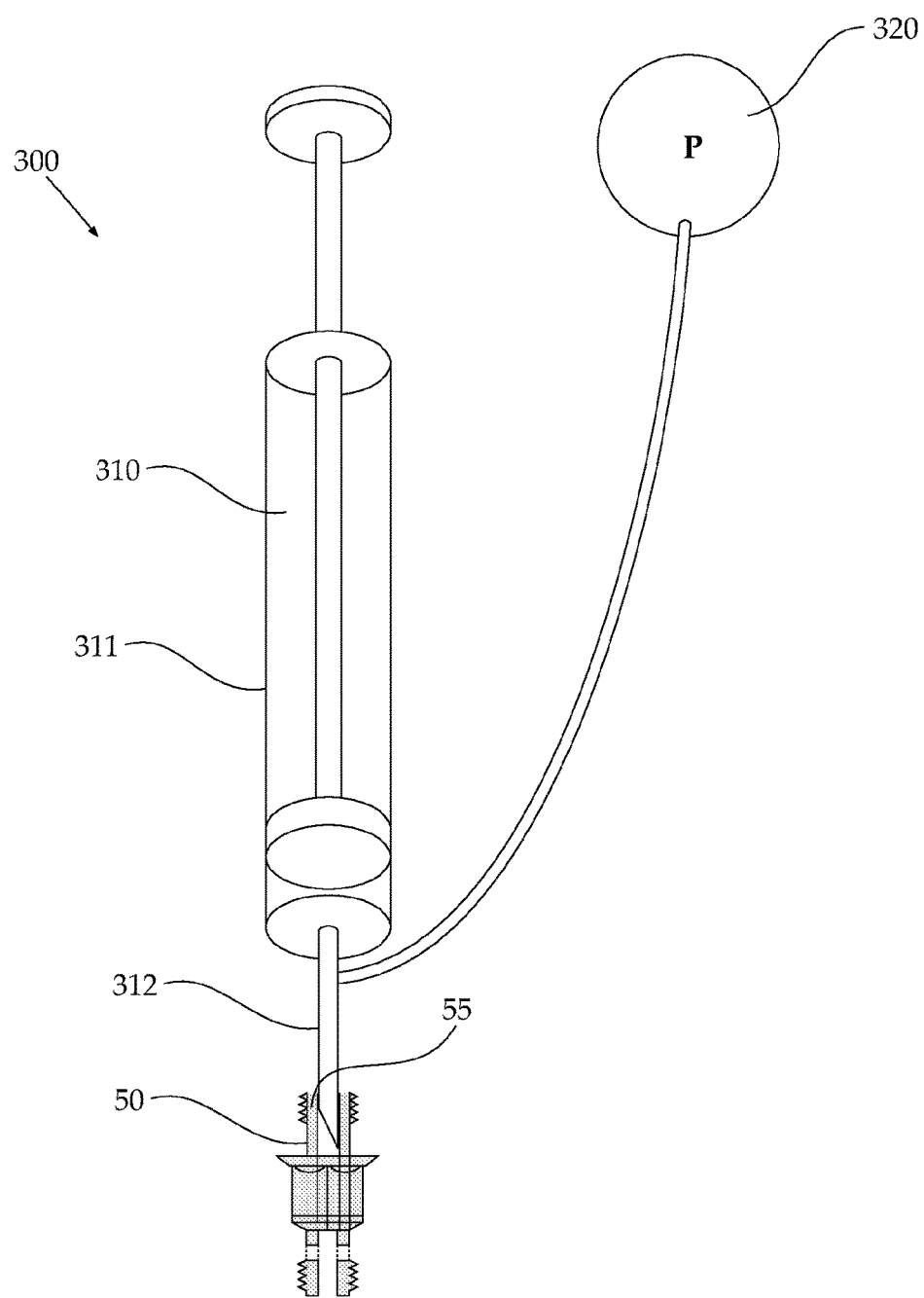
FIG. 28 schematically illustrates an injection system for injecting fluids through the system comprising a dental implant and directing element installed therein, according to some embodiments of the present invention.

Reference is now made to FIG. 28, which schematically illustrates an injection system 300 including a syringe tool 310 and a measuring device 320. Syringe 310 allows injecting pharmaceutical materials to the patient's tooth socket area through dental implant 10 or any other configuration of a dental implant that includes a multiplicity of openings through directing element 50 or any other type of a directing element secured thereto, to allow directing the pharmaceutical materials and/or any other fluidic material only to desired areas and/or locations in the socket by directing the material only through openings of the dental implant and directing element 50 that are unsealed by the directing element 50. Measuring device 320 allows controlling the pressure of injection by measuring the pressure on the fluid inside the syringe, for instance. Syringe 310 typically includes a needle 312 and a piston section 311 for allowing pressing down fluids from syringe 310 into directing element 50, through its opening 55.

Figure 29:
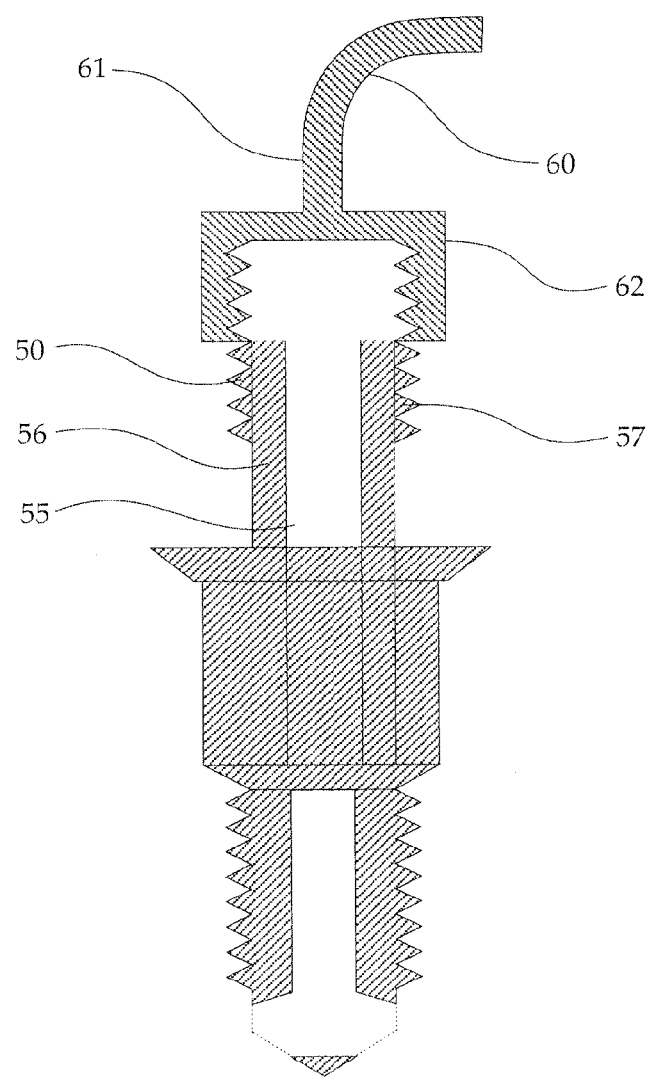
FIG. 29 schematically illustrates a portion of a threaded injection member for directing fluids through the system comprising a dental implant and directing element installed therein, according to additional or alternative embodiments of the present invention.
Figure 30:
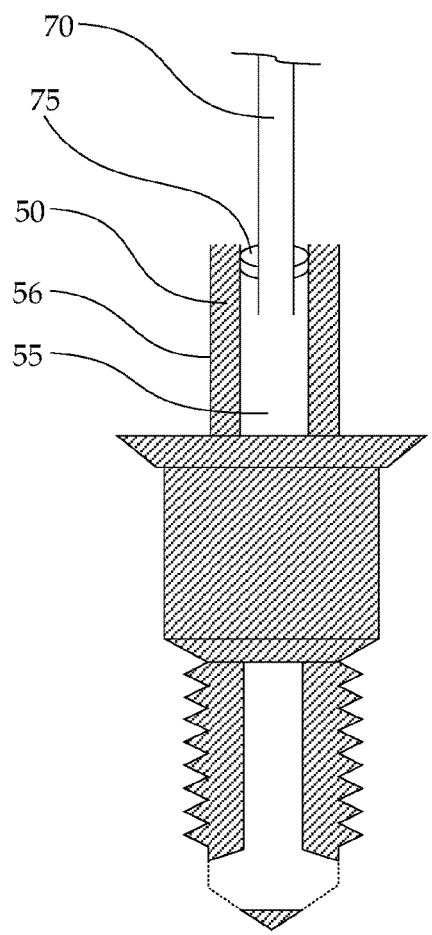
FIG. 30 schematically illustrate a portion of an internal gasket (or sealing member) for injection member for directing fluids through the system comprising a dental implant and directing element installed therein, according to additional or alternative embodiments of the present invention.
Figure 31:
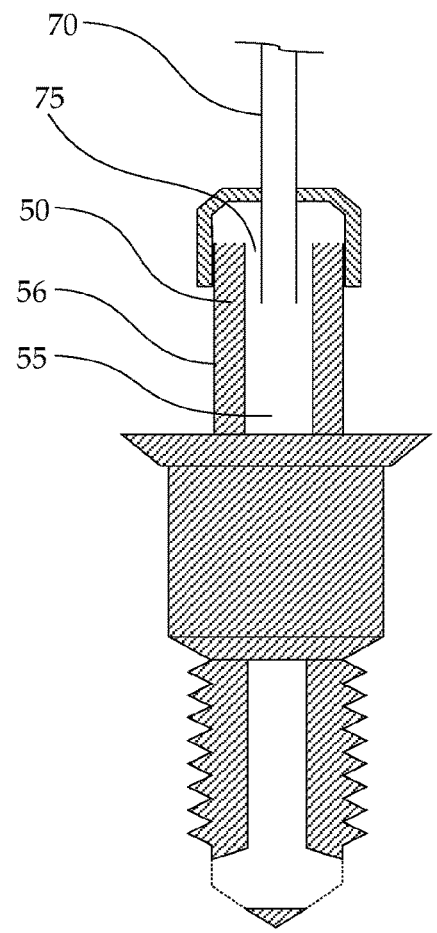
FIG. 31 schematically illustrate a portion of an external gasket (or sealing member) for injection member for directing fluids through the system comprising a dental implant and directing element installed therein, according to additional or alternative embodiments of the present invention.

Reference is now made to FIGS. 29-31, each representing a different interface between directing element 50 and an injection member of an injection tool of some sort for injecting fluids through the dental implant 10 and directing element 50, according to some embodiments of the present invention.

FIG. 29 shows a portion of an injection member 60 having a tube member 61 for directing fluids therefrom and a connecting member 62 connected to tube member 61 in one end and enables removably connection to the edge portion of an elongated section 56 of directing member 50. In this example, the external periphery of elongated section 56 includes a male screw thread portion 57, where connecting member 62 is a female screw thread portion configured to secure to male screw portion 57 for securing injection member 60 to directing element 50.

FIG. 30 shows a portion of a tube edge 70 of an injection tool for directing fluids therefrom that connects to the edge portion of elongated section 56 of directing member 50 through an internal sealing plug 75 that is configured to seal opening 55 of directing element 50 by being inserted therethrough. Internal sealing plug 75 can be made of a material having a sufficient elasticity for properly sealing opening 55 such as silicon, rubber, cork, etc.

FIG. 31 shows a portion of a tube edge 70 of an injection tool for directing fluids therefrom that connects to the edge portion of elongated section 56 of directing member 50 through an external sealing plug 78 that is configured to seal opening 55 of directing element 50 by hermetically covering thereof. External sealing plug 78 can be made of a material having a sufficient elasticity for properly sealing opening 55 such as silicon, rubber, cork, etc.

As illustrated, the injecting of fluids to the dental implant through the directing element may be through a mechanism that seals the circumference of the opening of the directing element allowing only a narrow passageway of a width that is substantially equal to the diameter of the tube or needle through which the fluid is injected. This may assist the caretaker (e.g. the dentist or any other person carrying out the implantation and/or injection procedure) in better controlling of the pressure of the injected fluid.

Figure 32:
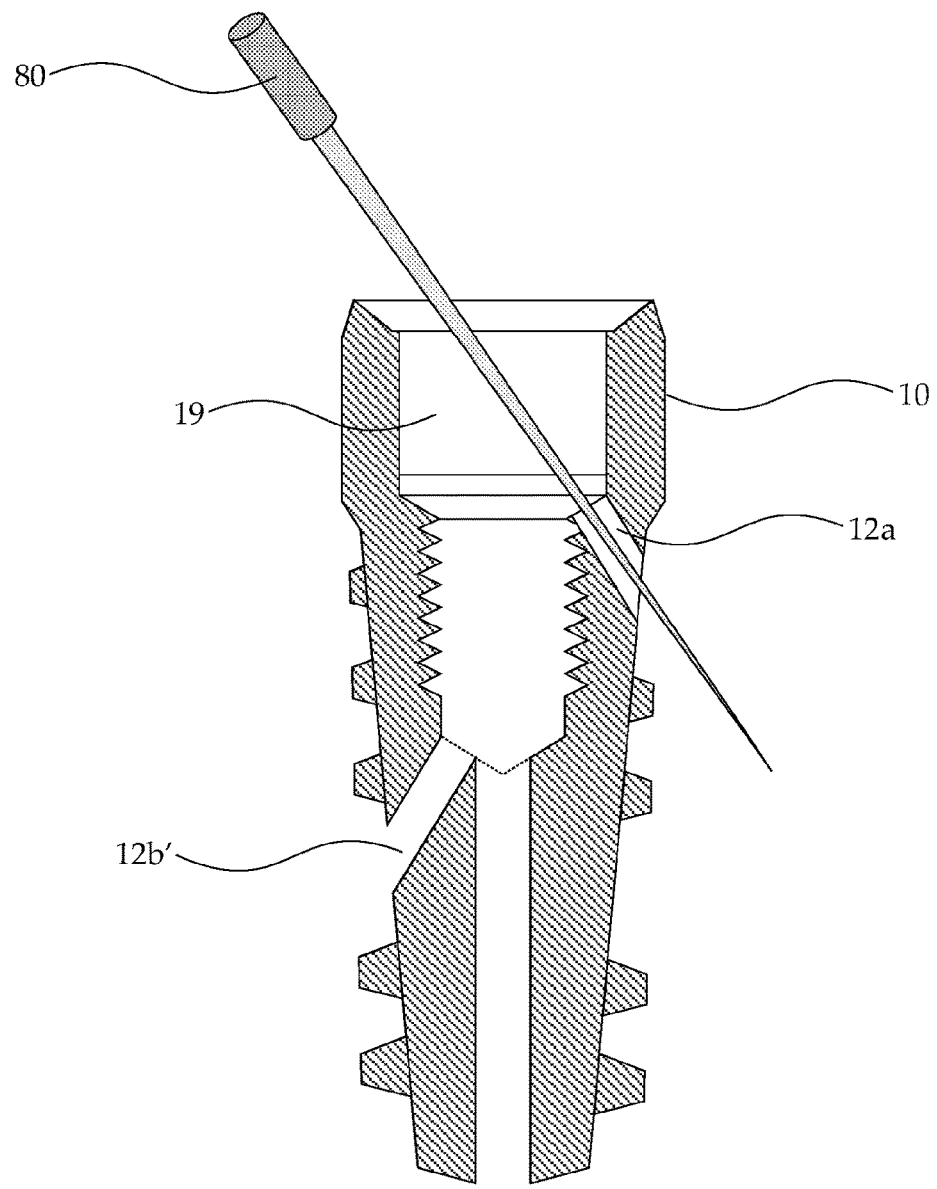
FIG. 32 schematically illustrates a dental tool such as a cleansing needle, an endodontic file, or dental ultrasonic scaling device etc. inserted through one of the channel shaped openings of the dental implant illustrated in FIG. 1.

Reference is now made to FIG. 32, schematically illustrating insertion of a dental cleansing needle 80 through one of the channel shaped openings 12a of dental implant 50 having the multiplicity of openings 19, 12a-12c and 12a'-12c', according to some embodiments of the present invention. This illustration exemplifies how channel shaped openings 12a-12c' allow insertion of other dental devices for other purposes such as for maintenance of dental implant 50 by, for instance, cleaning it using a dental cleansing needle 80, endodontic file or any other device. Other devices and other procedures may be utilized using the multiple openings of dental implant 50 and their configuration (e.g. the tilted channel configuration) for example, for sealing the openings 12a-12c' once the entire treatment is completed and the like. The cleaning of the channels can be carried out at a later date (even years later), whenever a problem (such as bone regression or peri-implantitis) occurs and/or whenever intervention is required to save the implant and prevent failure by bone filling or using medicament, for instance.

Figure 33:
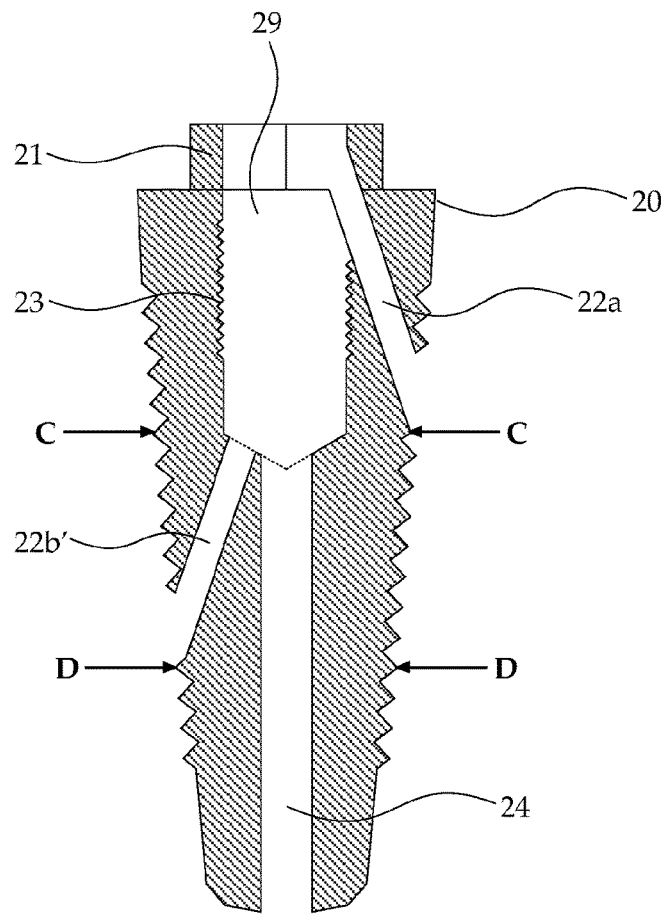
FIG. 33 is a transparent side view schematically illustrating a dental implant with a external hexagonal connection, which is a protruding edge portion, according to other embodiments of the invention.
Figure 34A:
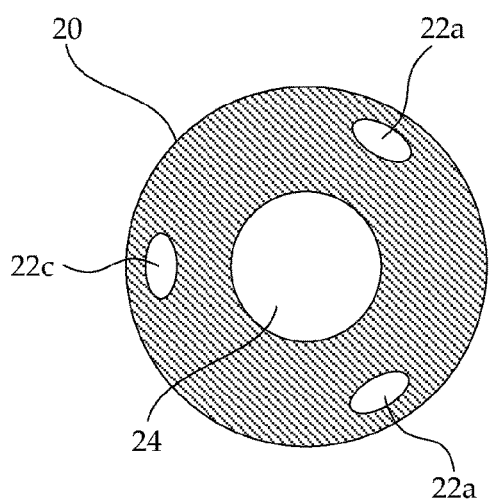
FIG. 34A is an elevated cross sectional view schematically illustrating cross section C-C of the dental implant of FIG. 33.
Figure 34B:
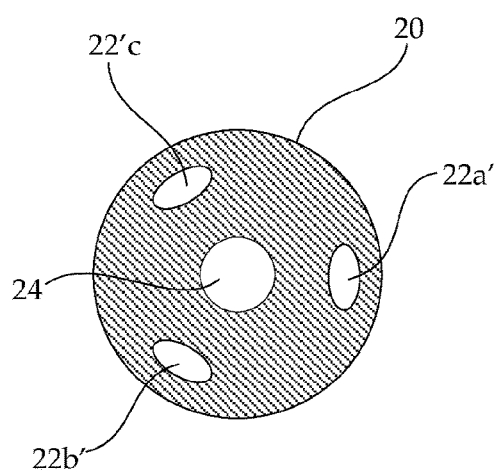
FIG. 34B is an elevated cross sectional view schematically illustrating cross section D-D of the dental implant of FIG. 33.
Figure 38:
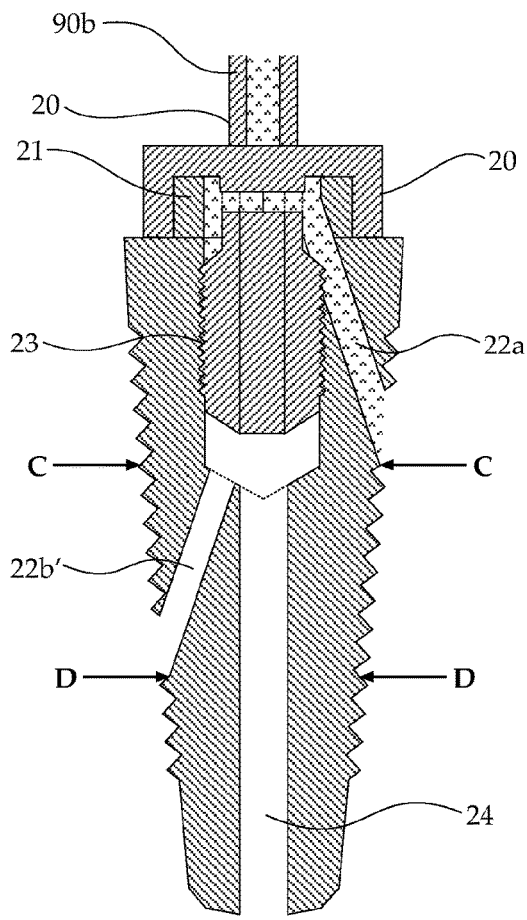
FIG. 38 is a transparent side view schematically illustrating the dental implant of FIG. 33 having a directing element secured thereto, according to some embodiments of the present invention.
Figure 39:
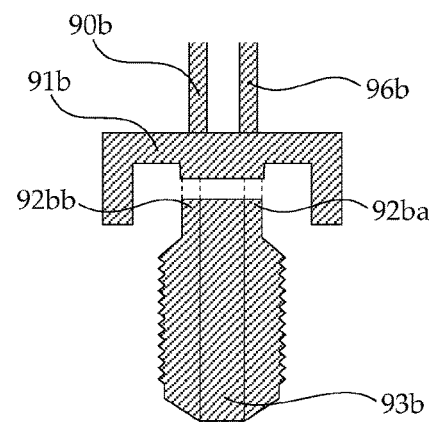
FIG. 39 is a side view schematically illustrating the directing element of FIG. 38, according to some embodiments of the present invention.
Figure 40A:
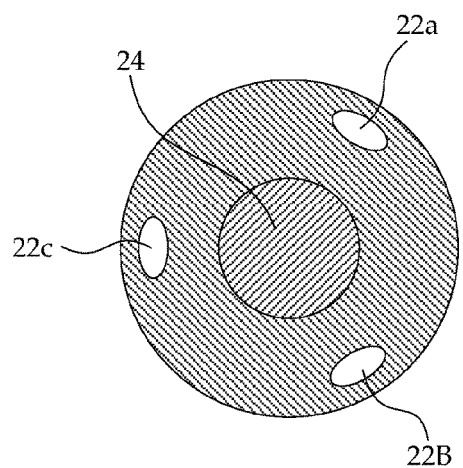
FIG. 40A is an elevated cross sectional view showing cross section C-C of the dental implant shown in FIG. 36 directing element secured thereto, according to some embodiments of the present invention.
Figure 40B:
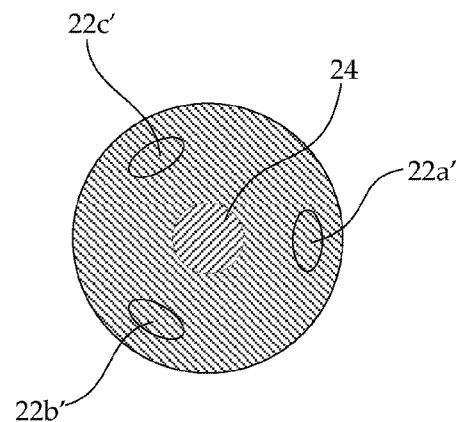
FIG. 40B is an elevated cross sectional view showing cross section D-D of the dental implant shown in FIG. 36 directing element secured thereto, according to some embodiments of the present invention.

Reference is now made to FIGS. 33, 34A and 34B, schematically illustrating a dental implant 20 with a main opening 29 edge portion having a protruding hexagonal shaped external connection, according to other embodiments of the present invention. The protruding hexagonal shape of the edge portion is designed for connecting to any one or more dental devices such as abutments and the like that include a compatible socket hexagonal portion that can connect to protruding hexagonal shaped main opening 29 portion. This is to illustrate the general notion that the design of the dental implant can be made according to any devices, tools and apparatuses available in the field to allow the implant to properly fit to connect to those available devices and/or tools.

Each directing elements is designed according to each design (shape, size and the like) of the specific dental implant they need to be secured to in addition to being designed according to the exact tooth and socket structure. For example for external hexagonal dental implants the directing element includes hexagonally shaped part (e.g. first part 51a) that is designed to fit and be received by the hexagonal opening portion of the implant. Each dental implant and/or each directing element may include one or more markings indicative of angular positions of one or more of the openings and/or sealed openings thereof. For example, dental implant 10 may include three marks (not shown) such as three lines imprinted upon an external surface thereof. Each line is indicative of angular positioning of each of openings 12a-12c and 12a'-12c', respectively, for allowing a user to direct devices such as a cleansing needle or an endodontic file, for instance, through the desired opening(s). Additionally or alternatively, the directing elements may also include markings such as imprinted lines, indicative of one or more positioning of the sealed openings of a dental implant the directing element is configured to fit.

As illustrated in FIGS. 33-35 and 37A-37B, dental implant 20 includes three main portions: a first portion 21, a second portion 23 and a third portion 24. First portion 21 includes a first part of the main opening 29 walled by an external hexagonal shaped protrusion. One or more tilted channels shaped openings such as openings 22a, 22b and 22c may extend from the opening of first portion 21 extending through and ending at second portion 23 of dental implant 20. Second portion 23 may include another part of the main opening 29. Second portion 23 may include a female screw thread walling the inner side thereof to allow receiving and connecting thereby to one or more devices such as abutments, bridges and the like and/or to directing elements. Other channel shaped tilted openings 22a', 22b' and 22c' may extend from the opening of second portion 23. Third portion 24 includes the third part of the main opening 29 extending from first and second portions 21 and 23.

FIGS. 35-37 show one configuration of a directing element 90a that can fit the design of dental implant 20 allowing all openings to be open when the directing element 90a is secured to dental implant 20. Directing element 90a includes a first section 91a having a hexagonal cover that fits to the hexagonal protrusion of first portion 21 and a second section 94a including one or more openings 92aa and 92ab configured to allow material flow to openings 22a-22c while leaving them open, and a main opening 24 extending from one edge of directing member 90a to another to allow leaving openings 22a'-22c' and 24 to be open when directing element 90a is secured to dental implant 20. First section 91a may further include an elongated neck portion 96a perforated to include an opening therein that extends all through directing element 90a. Second section 94a of directing element 90a may include an external male screw thread to allow being screwed to the female screw portion of second portion 23 of dental implant 20 thereby securing dental implant 20 and directing element 90a to one another.

Reference is now made to FIGS. 38-40B, schematically illustrating another type of directing element 90b that can be secured to dental implant 20, according to some embodiments of the present invention. Directing element 90b includes similar parts such as parts 96b, 91b and 92ba-92bc to those equivalent parts 96a, 91a and 92aa-92ac of directing element 90a with the exception that a second section 93b of directing element 90b is completely sealed to allow sealing openings 22a'/22c' and 24 of dental implant 20.

Reference is now made to FIGS. 41, 42, 43A and 43B, schematically illustrating yet another type of directing element 90c that can be secured to dental implant 20, according to some embodiments of the present invention. Directing element 90c includes similar parts such as parts 96c and 91c to those equivalent parts 96a and 91a of directing element 90a with the exception that a second section 92c of directing element 90c allows sealing openings 22a-22c of dental implant 20 and leaving openings 22a'-22c' and 24 open, when secured thereto.

Figure 44:
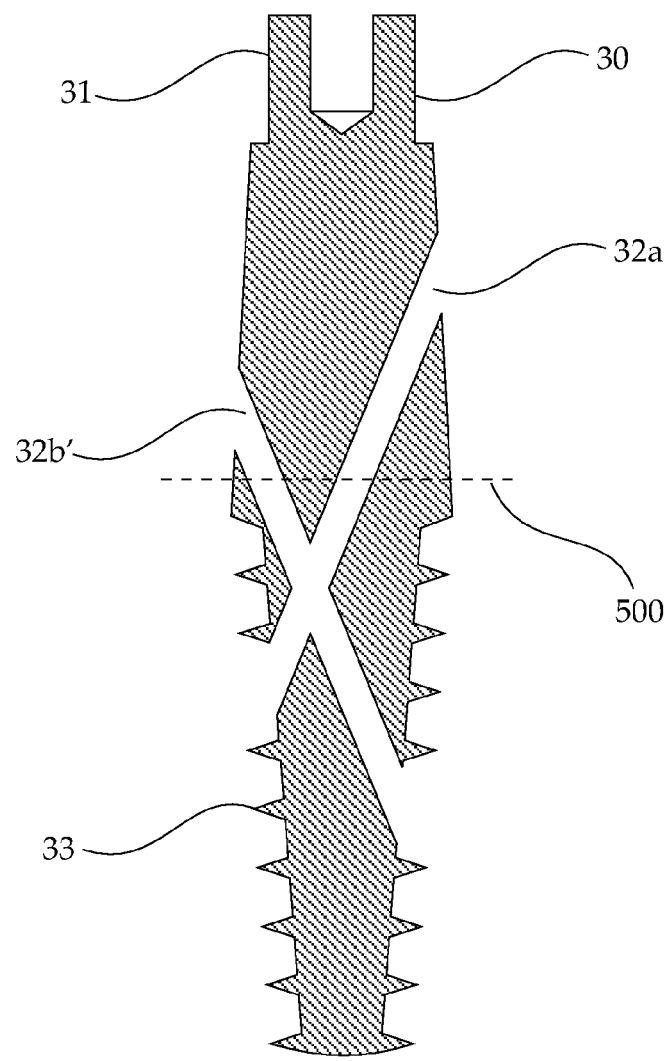
FIG. 44 schematically illustrates a dental implant having an abutment portion integrally connected thereto, according to some embodiments of the present invention.

Reference is now made to FIG. 44, which schematically illustrates a dental implant 30 having an abutment portion 31 integrally connected thereto, according to some embodiments of the present invention. Dental implant 30 includes a first portion 31 and a second portion 33. First portion 31 includes one or more protruding members that may be designed to secure to a tooth cap or to any other dental device/installation as known in the art. Dental implant 30 may include a multiplicity of openings such as openings 32a and 32b' over second portion 33 thereof, which have a tilted channel shape. Each opening may extend from a proximal surface of dental implant 30 that surfaces above or at a gum surface from which there is access to the inner parts of dental implant 30 and external distal parts for allowing a caretaker such as a dentist to inject materials by placing the syringe needle edge at the proximal end of each channel opening to allow fluids to reach the distal end of that channel for exiting the implant in the desired intra cavity area. In these configurations dental implant 30 does not have a main opening from which the channel shaped openings extend. Each channel can separately reach a different proximal end of dental implant 30.

The system may include one or more dental implants of one or more types, for example several sets of dental implants each set including several dental implants each fitting to be implanted to replace a different human tooth type, where each dental implant is associated with a set of directing element, each allowing sealing different openings of the same dental implant for allowing accessing different intra-cavity areas for adapting the filling process to the specific configuration of the specific tooth socket of the patient. This will allow, for example, filling different areas in tooth sockets of the same tooth type in different patients each requiring filling different spaces in the socket area with bone morphogenetic materials. This will also allow using different types of dental implants for the same tooth type for securing different installations configurations thereto, such as different abutments having different fastening configurations and/or means.

Figure 45:
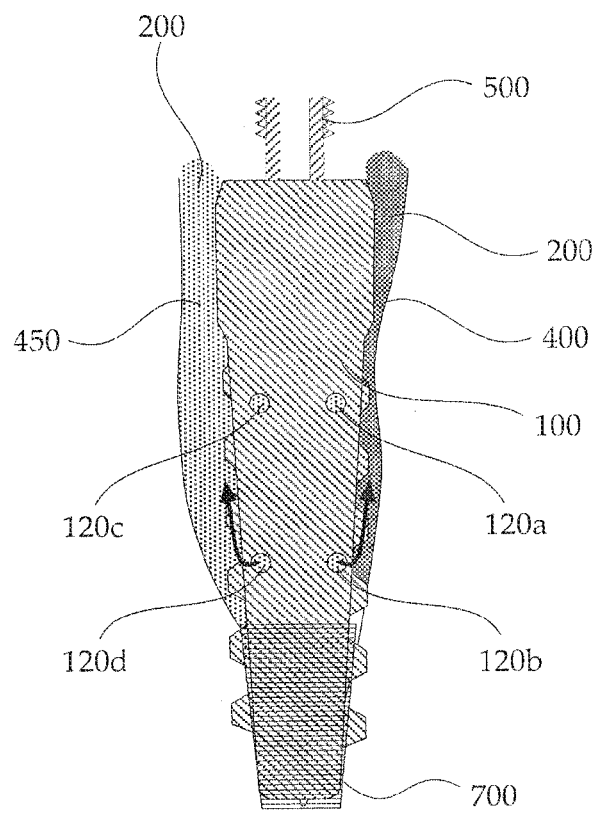
FIG. 45 schematically illustrates one intra cavity area of a patient having a dental implant and directing element implanted therein for allowing filling a space between an outer surface of a portion of the dental implant and a jaw bone of the patient, according to some embodiments of the present invention.
Figure 46:
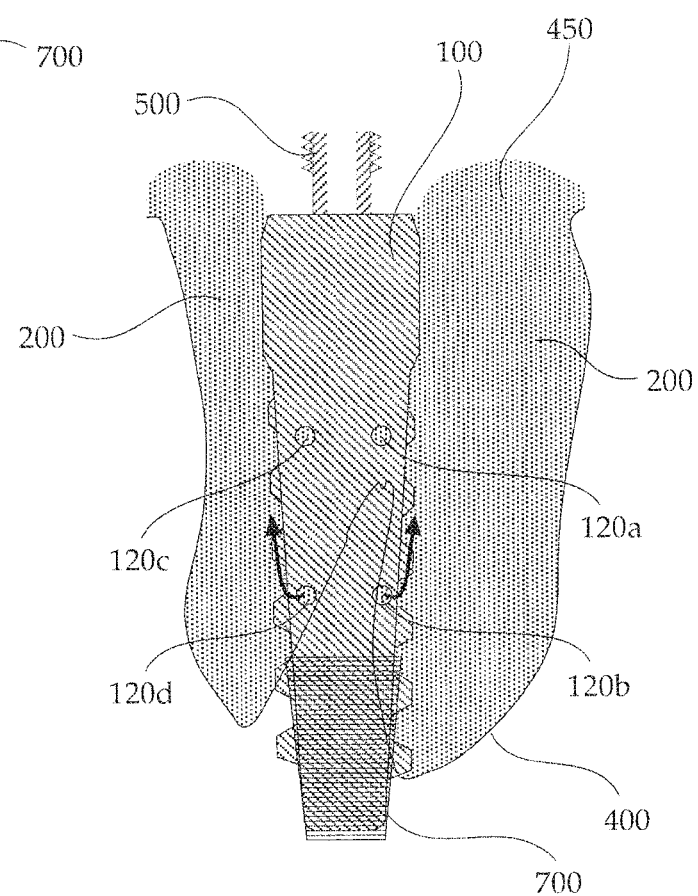
FIG. 46 schematically illustrates another intra cavity area of a patient having a dental implant and directing element implanted therein for allowing filling a space between an outer surface of a portion of the dental implant and a jaw bone of the patient, according to some embodiments of the present invention.

Reference is now made to FIGS. 45-46, schematically illustrating a process of injecting of bone morphogenetic filling material 200 into an intra-cavity area of a patient, to allow filling a space 450 between the outer surface of a portion of a dental implant 100 and a jaw bone 400 of the patient, according to some embodiments of the present invention. The filling material 200 is injected through a multiplicity of openings 120a-120d of dental implant 100 having a directing element 500 installed therein and secured thereto. A drilling zone 700 is drilled in the bone 400 of the patient to receive a distal portion of dental implant 100 therein.

In FIG. 45 there is significantly less space 450 between the bone 400 and the outer surface of the distal portion of dental implant 100 illustrated in FIG. 46.

As illustrated in FIGS. 45-46, once dental implant 100 is implanted in the jawbone of the patient, the fluids injected from the upper portion of dental implant 100 create pressure that allows the fluids (often jelly like fluid) to be pushed towards the tooth socket space 450. The filling material 200 is injected through openings such as openings 120a-120d of dental implant 100 under a predefined pressure that is within a predefined range to: (i) make sure that no unfilled spaces are left in space 450 and that all of space 450 is fully filled; and (ii) avoiding applying too much pressure on the walls of the bone 400 and/or implant 100 surface, which may destabilize dental implant's 100 positioning.

One optional objective of the dental implant configuration is to allow injecting substances through the implant 100 from its distal end outwardly towards the external proximal end of the implant for optimal filling of the space between outer surface of the implant and the jawbone, for instance. This means that if the distal openings (such as 12a'-12c') are accessible (open), the filling process will include first accessing through those openings and then through the proximal openings (such as openings 12a-12c).

According to some embodiments, implant 100 is filled with a fluid (e.g. a bone-constructive fluid), where the design of the implant and directing element installed therein, allows the fluid to flow outwardly from the distal opening closer to the gap between the implant and gum 460. This technique ensures that the spaces are fully filled by the fluid since the filling is carried out from the proximal to the distal end of the implant. This technique additionally allows immediate implantation of implant 100 after extraction of the tooth that implant 100 replaces allowing thereby avoiding another commonly used chirurgical procedure of bone construction that is typically carried out prior to the implantation.

Figure 47:
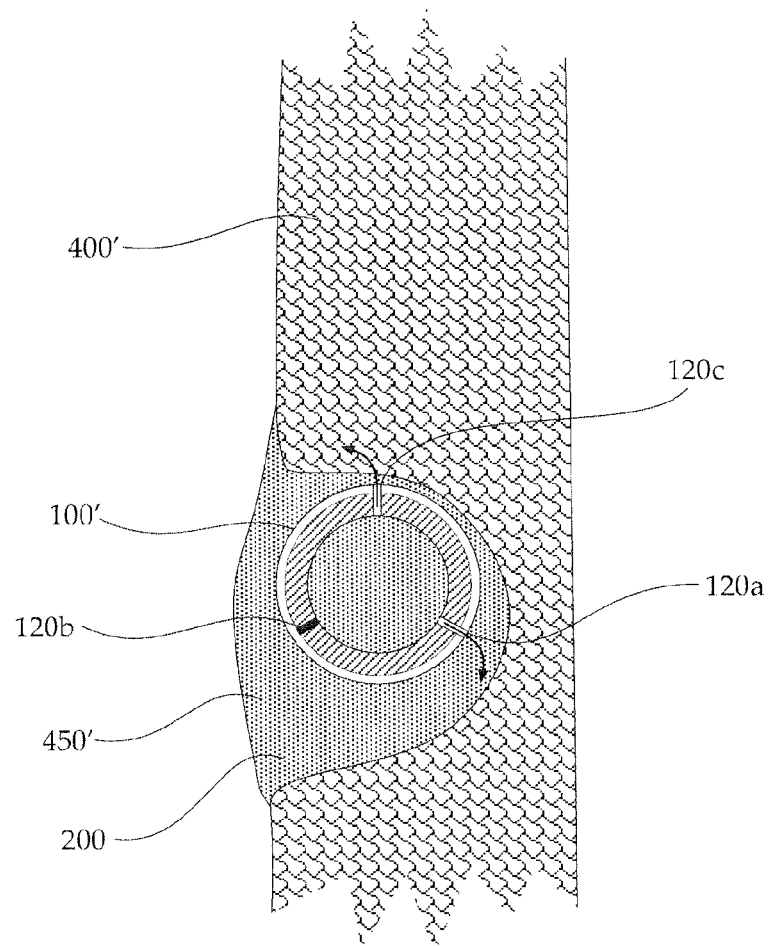
FIG. 47 an elevated cross sectional view of another intra cavity area of a patient having a dental implant and directing element implanted therein for allowing injecting bone building materials to a tooth socket area where buccal or lingual bone plate is missing, according to some embodiments of the present invention.

FIG. 47 is a cross sectional view of another dental implant 100' implanted in another type of a tooth socket of a patient, where the filling material 200 is injected to fill a space 450' between the alveolar bone 400' and the outer surface of dental implant 100', according to some embodiments of the present invention. The filling material 200 is injected through the directing element and openings such as openings 120a and 120c of dental implant 100' under a predefined pressure to make sure that the filling of space 450' is done in an optimal manner Once opening 120b may be sealed to allow directing the fluids only through desired openings such as 120a and/or 120b. In the case illustrated in FIG. 47, in one side of the tooth socket in which dental implant 100' is implanted, there is no bone walling space, buccal or lingual, 450'.

The configuration of the system including the dental implants and directing elements may allow removing a damaged tooth to be replaced and carrying out implantation in the tooth socket of that very tooth in the same procedure/session meaning substantially one right after the other also in cases requiring bone-implant or bone osteogenesis. This procedure may replace chirurgical procedures for bone implanting by allowing injecting bone building materials through the openings of the implant using the directing element to direct the material to desired locations in the tooth socket. This procedure may additionally improve anchoring of the implant inside the jawbone when very little jawbone is available. The anchoring is improved by allowing using the limited jawbone available for an initial anchoring of the implant and then increasing jawbone surface and depth by building bone tissue using the bone building gel injection procedure.

The configuration of the system including the dental implant and directing element may additionally facilitate in allowing combining dental implantation in the maxilla and sinus floor lifting and/or augmentation by allowing to insert bone grafting materials to the sinus membrane area through the implanted dental implant using the multiple openings thereof as well as one or more of compatible directing elements secured thereto.

The insertion of the material such as the bone grafting material to the space between the outer surface of the implant and jawbone in the intra-cavity area of the patient (the jawbone socket of the implant) may carried out immediately after the implant is installed at the same dental treatment session. This is referred to as an "immediate implantation" procedure, in which the bone-grafting material or any other material is directed through the openings of the dental implant that are open through the directing element secured thereto, to optimize and expedite the dental treatment. In current dental implant treatments the jawbone in the cavity area in which the implant is to be installed is often in a receded state requiring removing a damaged tooth for replacing it with the implant, recovering the area from the removal of the tooth, bone grafting and then implanting the implant. The dental implant of the present invention is configured to allow carrying out all these procedures in the same dental treatment session.

The system also allows reopening the sealers of the dental implant after a substantial time period such as after a few years for treating various dental conditions by easily accessing the space between the outer surface of the implant and the jawbone area. For example, jawbone may recede or absorb over the years long after the implant is installed. The implant of the present invention, therefore allows reopening thereof for directing bone grafting materials to treat this problem using one or more suitable directing elements to direct the bone-grafting material to those areas behind the implant in which the bone has receded. In this case, the one or more suitable directing elements are used at that later stage.

Figure 48:
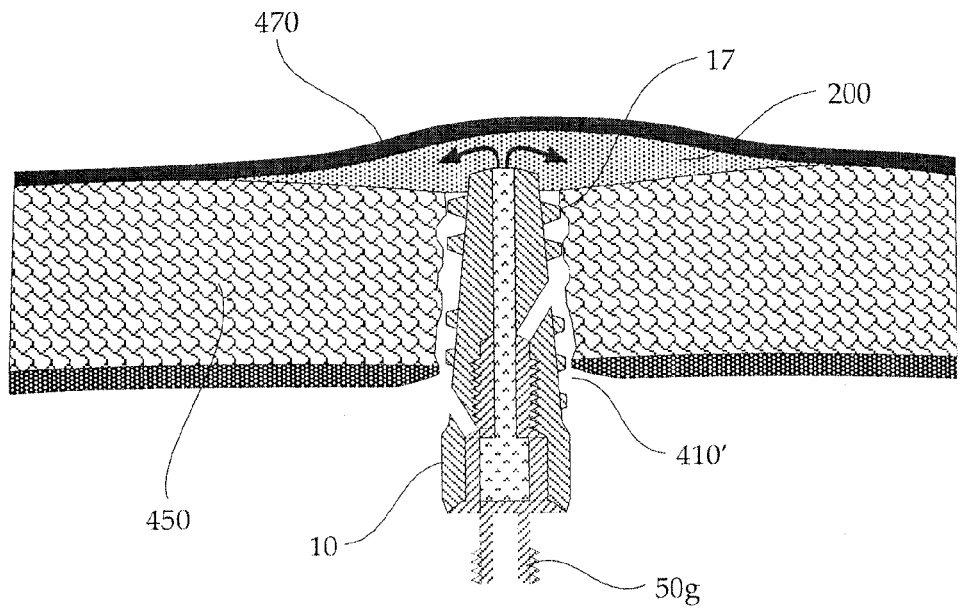
FIG. 48 schematically illustrates a dental implant having a directing element secured thereto used in a first stage of a procedure of maxillary sinus floor lifting and augmentation, according to some embodiments of the present invention.
Figure 49:
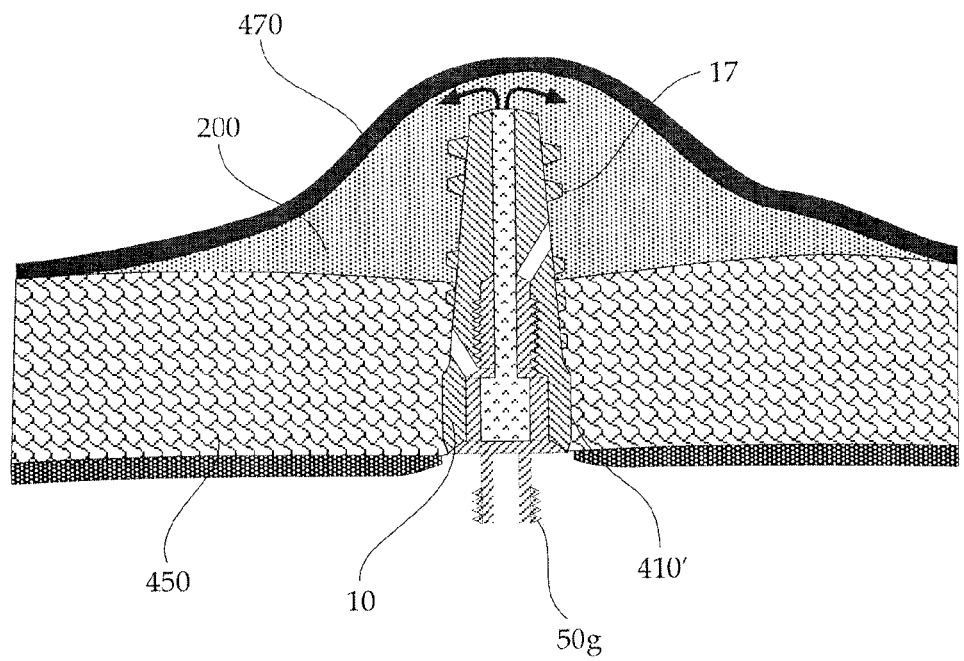
FIG. 49 schematically illustrates the dental implant having the directing element secured thereto used in a second stage of the maxillary sinus floor lifting and augmentation procedure, according to some embodiments of the present invention.

FIGS. 48-49 illustrate dental implant 10 having a directing element 50g secured thereto used in a procedure of maxillary sinus floor lifting and augmentation, according to some embodiments of the present invention, wherein FIG. 48 illustrates a first stage in the procedure and FIG. 49 illustrates a second stage.

As shown in FIGS. 48-49, dental implant 10 is implanted in the maxilla bone 450 of a bore 410' threaded inside a patient's maxilla having directing element 50g secured thereto. In one of the initial stages, dental implant 10 is not inserted all the way through bore 410' where an initial space between the sinus membrane 470 and a distal end of dental implant 10 can be filled with bone grafting materials 200 to lift the membrane and/or increase its width. The bone grafting material 200 continues to be inserted allowing dental implant 10 to be screwed deeper and deeper into bore 410' until it flushes with the surface of bore 410', as illustrated in FIG. 49 and until the membrane 470 is lifted or widened to the desired size/location. For example an outer threaded portion 17 may be a male screw thread designed suitable for being screwed in bore 410'. These stages can be repeated any number of times required for completing the medical procedure, wherein at each stage the bore is deepened a little further allowing inserting the dental implant 10 further deep therein.

Some sinus floor lifting and augmentation procedures require inserting other instruments or object through the dental implant such as inserting special balloons to the sinus membrane area and then filling the balloon with air for lifting the sinus floor or inserting any other materials in this process. The air filling and optionally also the insertion of the balloon may be made through one or more of the implant's openings using one or more of the compatible directing elements such as shown in FIGS. 48-49, to access the membrane area.

Directing element 50g may seal all openings 12a-12c and 12a'-12c' while only main opening 14 is open to allow flow from the distal end 14 closer to the sinus membrane.

Figure 50:
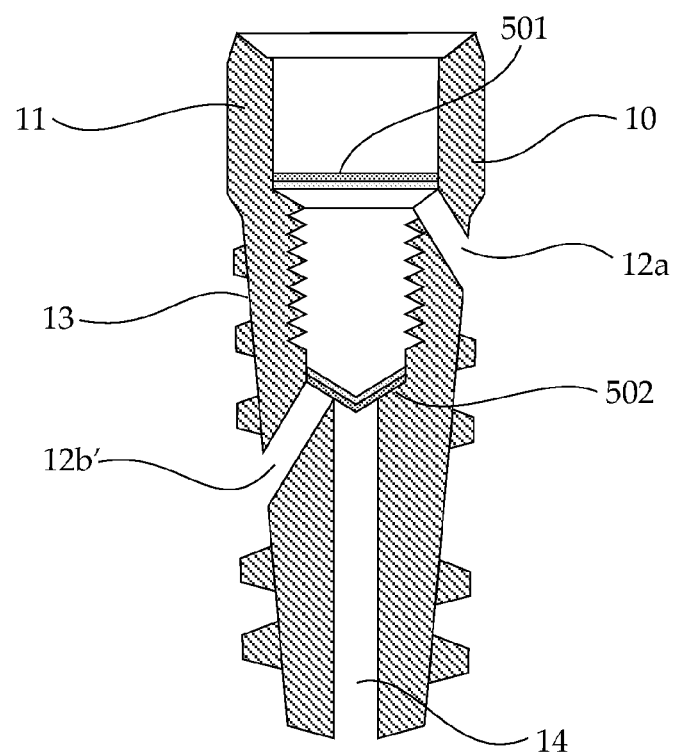
FIG. 50 schematically illustrates a dental implant having various sealers configured for sealing different openings thereof, according to some embodiments of the present invention.

FIG. 50 schematically illustrates various sealers such as a first sealer 501 (also shown in FIG. 51) and a second sealer 502 for dental implant 10, each sealer is configured for sealing different openings of dental implant 10, according to some embodiments of the present invention. As illustrated, first sealer 501 is a ring, configured in shape, thickness and size to seal openings 12a-12c in first portion 11 of main opening 19. In the same manner second sealer 502 is configured for sealing openings 12a'-12c'. The sealers 501 and 502 may be used for permanent sealing, after the materials (e.g. bone morphogenetic materials) have been injected for preventing infection.

The sealers 501 and 502 may be a double layer plate made of a first rigid material such as a rigid metal and a more elastic material connected thereto as a second layer such as rubber or dried glue. The directing element can be used, after specific modifications as a transfer unit and/or capping device and/or abutment and/or mesostructure and/or elongation unit and or an implant carrier.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments.

Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a sub-combination or variation of a sub-combination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what essentially incorporates the essential idea of the invention.

Although the invention has been described in detail, nevertheless changes and modifications, which do not depart from the teachings of the present invention, will be evident to those skilled in the art. Such changes and modifications are deemed to come within the purview of the present invention and the appended claims.

What is claimed is:

1. A dental implant system for accessing selected intra-cavity spaces, said system comprising:
 a dental implant configured to be implanted in a patient's jawbone, the dental implant having a main opening, which exposes a cavity extending along a longitudinal insertion axis of the dental implant, wherein the cavity has at least four sections: a first, multi-sided section proximal to the main opening and configured to receive a dental abutment or cap; a second, tapered section; a third, threaded section; and an end section, distal to the main opening, wherein the second, tapered section forms a juncture between the first and the third section, wherein a plurality of channel openings extend through the tapered section at an angle of less than 90 degrees to the insertion axis, said channel openings providing access to an intra-cavity space from the main opening when the dental implant is implanted; and
 at least one directing element configured to fit in the cavity to block access to at least one of the plurality of channel openings, while allowing access to the intra-cavity space through at least one other of the plurality of channel openings, wherein the at least one directing element comprises two distinct parts, a first part being multi-sided to fit the first section of the cavity, and the second part being threaded to fit the third section of the cavity.

2. The dental implant system according to claim 1, wherein the at least one directing element comprises a plurality of directing elements configured to fit in the cavity, wherein each of the plurality of directing elements is configured to seal a different subset of the plurality of channel openings.

3. The dental implant system according to claim 1, wherein said dental implant comprises an outer threaded portion to grip the intra-cavity space.

4. The dental implant system according to claim 1, further comprising a plurality of sealers for sealing each of the plurality of channel openings, and wherein each sealer comprises a double layer plate made of a first layer comprising a first rigid material and a second layer comprising a second material that is more elastic than the first material and has sealing capabilities to prevent infection.

5. The dental implant system according to claim 1, wherein the directing element further comprises a connector to an instrument for injecting pharmaceutical materials to the intra-cavity space through at least one of the plurality of channel opening.

6. The dental implant system according to claim 5, wherein the directing element further comprises a second connector to a pressure controlling mechanism for measuring and controlling the pressure of injection.

7. A method of accessing an intra-cavity space of a patient's jawbone, said method comprising:
 installing a dental implant in a patient's jawbone, the dental implant having a main opening, which exposes a cavity extending along a longitudinal insertion axis of the dental implant, wherein the cavity has at least four sections: a first, multi-sided section proximal to the main opening and configured to receive a dental abutment or cap; a second, tapered plane section, wherein a plurality of channel openings extend through the tapered section at an angle of less than 90 degrees to the axis of the main opening, said channel openings allowing access to the intra-cavity space from the main opening;
 securing a directing element in the cavity of the dental implant, said directing element configured to block access to at least one of the plurality of channel openings, while allowing access to the intra-cavity space through at least one other of said plurality of channel openings, carrying out a dental procedure requiring access to the intra-cavity space; and
 removing said directing element once the dental procedure is completed.

8. The method according to claim 7, wherein the dental procedure comprises directing a material through the directing element to the intra-cavity space.

9. The method according to claim 8, wherein said material comprises one or more of a bone-grafting material for enhancing bone-building, an infection or disease therapy material, and a cleansing fluid.

10. The method according to claim 8, further comprising measuring and controlling injected pressure of the material directed through the directing element.

11. The method according to claim 8, wherein said directing of the material comprises one of:
 Injecting the material by directing an injection tool through the directing element to the at least one other of the channel openings; or
 injecting the material through said directing element under controlled pressure such that the material enters the directing element before reaching the intra-cavity space.

12. The method according to claim 8, wherein directing the material is performed immediately after installing the dental implant.

13. The method according to claim 8, wherein said directing of the material is performed some time after the dental implant is installed.

14. The method according to claim 7, further comprising cleansing the plurality of channel openings by directing a mechanical cleansing device through at least one of the channel openings after the directing element has been removed.

15. The method according to claim 7, wherein said dental implant is installed in a maxilla bone and the procedure comprises treating a sinus membrane.

16. The method according to claim 15, wherein the dental implant is inserted into a bore of the maxilla bone and wherein a bone-grafting material is inserted through the directing element and through the at least one other of the plurality of channel openings to lift the sinus membrane.

17. The method according to claim 7, further comprising sealing the dental implant after the directing element is removed by using a plurality of sealers for sealing the plurality of channel openings, wherein each sealer comprises a double layer plate made of a first layer comprising a first rigid material and a second layer comprising a material that is more elastic than said first material.

* * * * *